(12) United States Patent
Chen et al.

(10) Patent No.: US 10,780,030 B2
(45) Date of Patent: *Sep. 22, 2020

(54) CARBONATED COSMETIC PRODUCTS CONTAINING POLYMERS

(71) Applicant: L'OREAL, Paris (FR)

(72) Inventors: Michell Chen, Tokyo (JP); Gloria Frimpong Allorbi, Parsippany, NJ (US); Anand Mahadeshwar, Scotch Plains, NJ (US)

(73) Assignee: L'OREAL, Paris (FR)

(*) Notice: Subject to any disclaimer, the term of this patent is extended or adjusted under 35 U.S.C. 154(b) by 261 days.

This patent is subject to a terminal disclaimer.

(21) Appl. No.: 14/447,926

(22) Filed: Jul. 31, 2014

(65) Prior Publication Data

US 2016/0030307 A1 Feb. 4, 2016

(51) Int. Cl.
*A61K 8/19* (2006.01)
*A61K 8/362* (2006.01)
*A61Q 5/06* (2006.01)
*A61K 8/81* (2006.01)
*A61K 8/365* (2006.01)

(52) U.S. Cl.
CPC ............... *A61K 8/19* (2013.01); *A61K 8/365* (2013.01); *A61K 8/8147* (2013.01); *A61Q 5/06* (2013.01)

(58) Field of Classification Search
None
See application file for complete search history.

(56) References Cited

U.S. PATENT DOCUMENTS

| | | | |
|---|---|---|---|
| 2,047,398 A | 7/1936 | Voss et al. | |
| 2,723,248 A | 11/1955 | Wright | |
| 3,589,578 A | 6/1971 | Kamphausen | |
| 3,836,537 A | 9/1974 | Boerwinkle et al. | |
| 3,966,403 A | 6/1976 | Papantoniou et al. | |
| 3,966,404 A | 6/1976 | Papantoniou et al. | |
| 3,990,459 A | 11/1976 | Papantoniou | |
| 4,031,307 A | 6/1977 | DeMartino et al. | |
| 4,128,631 A | 12/1978 | Lundmark et al. | |
| 4,131,576 A | 12/1978 | Iovine et al. | |
| 4,137,208 A | 1/1979 | Elliott | |
| 4,693,935 A | 9/1987 | Mazurek | |
| 4,728,571 A | 3/1988 | Clemens et al. | |
| 4,972,037 A | 11/1990 | Garbe et al. | |
| 5,162,410 A | 11/1992 | Sweet | |
| 5,538,717 A | 7/1996 | de la Poterie | |
| 6,166,093 A | 12/2000 | Mougin et al. | |
| 6,395,265 B1 | 5/2002 | Mougin et al. | |
| 6,503,493 B1 | 1/2003 | Cardoso Dias | |
| 6,689,223 B1 * | 2/2004 | Meine ............... | C11D 1/8305 134/2 |
| 7,094,842 B2 | 8/2006 | Lennon | |
| 7,790,148 B2 | 9/2010 | Bui et al. | |
| 2005/0201961 A1 | 9/2005 | Lu et al. | |
| 2006/0013791 A1 | 1/2006 | Shimizu et al. | |
| 2007/0093619 A1 | 4/2007 | Bui et al. | |
| 2008/0219942 A1 * | 9/2008 | Chambers ............... | A61K 8/19 424/70.2 |
| 2010/0297050 A1 | 11/2010 | Bui et al. | |
| 2011/0189117 A1 | 8/2011 | Ferrari et al. | |
| 2015/0150782 A1 * | 6/2015 | Johnson ............... | A61K 8/97 424/70.21 |

FOREIGN PATENT DOCUMENTS

| | | | | |
|---|---|---|---|---|
| DE | 2330956 | | 1/1974 | |
| DE | 19849218 A1 * | | 4/2000 | ............... A61K 8/68 |
| EP | 080976 A1 | | 6/1983 | |
| EP | 412704 A2 | | 2/1991 | |
| EP | 412707 A1 | | 2/1991 | |
| EP | 582152 A2 | | 9/1994 | |
| EP | 619111 A1 | | 10/1994 | |
| EP | 637600 A1 | | 2/1995 | |
| EP | 640105 A1 | | 3/1995 | |
| EP | 648485 A1 | | 4/1995 | |
| EP | 656021 A1 | | 6/1995 | |
| EP | 751162 A1 | | 1/1997 | |
| FR | 1222944 | | 6/1960 | |
| FR | 1400366 | | 4/1965 | |
| FR | 1564110 | | 3/1969 | |
| FR | 1580545 | | 7/1969 | |
| FR | 2265781 | | 10/1975 | |
| FR | 2265782 | | 10/1975 | |
| FR | 2350384 | | 12/1977 | |
| FR | 2357241 | | 2/1978 | |
| FR | 2439798 | | 5/1980 | |
| FR | 2743297 A1 | | 7/1997 | |
| FR | 2953712 A1 | | 6/2011 | |
| GB | 839805 | | 6/1960 | |
| GB | 922457 | | 4/1963 | |
| GB | 1021400 | | 3/1966 | |
| GB | 1169862 | | 11/1969 | |
| GB | 1231452 | | 5/1971 | |
| GB | 2034724 A | | 6/1980 | |
| GB | 2506692 A | | 4/2014 | |
| JP | 2004043356 A | | 12/2004 | |

(Continued)

OTHER PUBLICATIONS

U.S. Appl. No. 14/447,926, filed Jul. 31, 2014, Chen et al.

(Continued)

*Primary Examiner* — Brian Gulledge
(74) *Attorney, Agent, or Firm* — Polsinelli PC

(57) ABSTRACT

Disclosed are compositions comprising at least one bicarbonate compound, at least one acid, at least one film forming polymer, and at least one cosmetically acceptable carrier, wherein the weight ratio of the at least one bicarbonate compound to the at least one acid is greater than or equal to about 1:1, and methods of altering the shape of keratin fibers comprising contacting the fibers with the compositions.

20 Claims, No Drawings

(56) References Cited

FOREIGN PATENT DOCUMENTS

| | | | |
|---|---|---|---|
| JP | 2011001282 A | | 6/2011 |
| JP | 2014-114264 | | 6/2014 |
| KR | 20100105168 A | * | 9/2010 |
| KR | 20100105168 A | * | 9/2010 |
| WO | 93/23009 A1 | | 11/1993 |
| WO | 93/23446 A2 | | 11/1993 |
| WO | 94/03510 A1 | | 2/1994 |
| WO | 95/00578 A1 | | 1/1995 |
| WO | 2004/073626 A2 | | 9/2004 |
| WO | WO 2008003686 A1 * | 1/2008 | ............... A61K 8/19 |
| WO | 2011/069786 A2 | | 6/2011 |
| WO | 2013/050398 A2 | | 4/2013 |
| WO | 2014/072490 A1 | | 5/2014 |

OTHER PUBLICATIONS

U.S. Appl. No. 14/447,946, filed Jul. 31, 2014, Chen et al.
European Examination Search Report dated Apr. 19, 2018 for corresponding Application No. EP 15744244.3.

* cited by examiner ously and unexpectedly, the applicants have discovered that combining a carbonated system comprising a bicarbonate compound and an acid with high levels of

CARBONATED COSMETIC PRODUCTS CONTAINING POLYMERS

TECHNICAL FIELD

The present disclosure relates to cosmetic compositions for keratinous substrates comprising at least one bicarbonate, at least one acid, at least one film forming polymer and at least cosmetically acceptable carrier.

BACKGROUND OF THE INVENTION

The use of polymers in cosmetic products for application onto keratinous substrates such as skin and hair is known. For example, film forming polymers are generally employed in products used to shape or style keratin fibers, such as hair. Higher levels of film forming polymers in cosmetic products can result with improved cosmetic properties such as higher degrees of shaping or styling hold on the hair which is desired by consumers. The results obtained, however, may be accompanied by a formation on the surface of keratinous substrates of unattractive residues in the form of whitish particles due to high levels of polymers in cosmetic products. The use of high levels of polymer may also result in an undesirable sticky or tacky product, which is difficult to apply to a substrate and does not evenly distribute on the fibers. Accordingly, it would be desirable to have a composition using high levels of film forming polymers that does not generate such unattractive residues or which do not result in a sticky, difficult product application and uneven distribution on the substrates.

Surprisingly and unexpectedly, the applicants have discovered that combining a carbonated system comprising a bicarbonate compound and an acid with high levels of polymer resulted in a solution to the above presented problems, thereby yielding a composition that exhibits high shaping or styling hold properties when applied on keratin fibers such as hair. The current invention also allows for easy shaping of the fibers and can lead to an excellent level of fixing of the hair in a desired configuration. When the keratin fibers comprise human hair on the head, the current invention allows for easy shaping of the hair to achieve a desired hair style and hold that last throughout the day or even for several days (i.e., longer lasting hold and/or longer lasting curl), while also imparting to the hair, good resistance to moisture or humidity and anti-frizz properties. Moreover, the composition of the present invention is easy to remove from the keratin fibers by shampooing or rinsing with water or with a cosmetically acceptable remover. It was surprising that even with the presence of high levels of film forming polymers in the composition, the current invention makes it possible to avoid the formation on the keratin fibers of unattractive whitish particles. In addition, the compositions of the current invention provide a touchable strong hold, added shine, and added volume to keratin fibers. The compositions also exhibit fast drying time on the keratin fibers. The compositions of the current invention also provide a clean and natural feel, no tacky feel, and no flaking.

BRIEF SUMMARY OF THE INVENTION

The present invention relates to a cosmetic composition, comprising:
a) at least one bicarbonate compound;
b) at least one acid;
c) at least one film forming polymer; and
d) at least one cosmetically acceptable carrier;
wherein the weight ratio of the at least one bicarbonate compound (a) to the at least one acid (b) is greater than or equal to about 1:1.

The invention also relates to an aqueous hair gel cosmetic composition comprising:
a) sodium bicarbonate;
b) at least one acid;
c) at least one film forming polymer;
d) a cosmetically acceptable carrier selected from water and water/organic solvent mixture;
e) optionally, at least one emulsifier; and
f) optionally, at least one rheology modifier;
wherein the weight ratio of the at least one bicarbonate (a) to the at least one acid (b) ranges from greater than about 1:1 to about 2:1.

The invention also relates to a hair cosmetic composition comprising:
a) sodium bicarbonate;
b) at least one acid;
c) at least one film forming polymer;
d) a cosmetically acceptable carrier selected from water and water/organic solvent mixture;
e) at least one propellant;
f) optionally, at least one emulsifier; and
g) optionally, at least one rheology modifier;
wherein the weight ratio of the at least one bicarbonate (a) to the at least one acid (b) ranges from greater than about 1:1 to about 3:1.

The present invention also relates to methods of making up or enhancing the appearance of keratin fibers, such as hair, said methods involving applying onto the fibers any one of the above-described compositions. In particular, the present invention relates to a method of styling hair involving applying to the hair any one of the above-described compositions.

DETAILED DESCRIPTION OF THE INVENTION

It has been unexpectedly discovered that a cosmetic composition comprising at least one bicarbonate compound, at least one acid, at least one film forming polymer and at least one cosmetically acceptable carrier provides enhanced styling or shaping and excellent styling hold properties on keratin fibers such as hair.

Without being bound by theory, it is believed that combinations of a bicarbonate compound and an acid such as citric acid or lactic acid at certain weight ratios to each other provide compositions containing high levels of film forming polymers that impart stronger films or coatings on the surface of keratin fibers such as hair and exhibit no or reduced flaking on the fibers.

The composition of the present invention is particularly useful as a hair gel composition.

The composition of the present invention is also particularly useful as an aerosolized hair cosmetic composition such as a hair mousse composition or hair spray composition when the composition contains at least one propellant.

As used herein, the expression "at least one" means one or more and thus includes individual components as well as mixtures/combinations.

It is also to be understood that, as used herein the terms "the," "a," or "an," mean "at least one," are understood to encompass the plural as well as the singular and should not be limited to "only one" unless explicitly indicated to the contrary. Thus, for example, the use of "an acid" is intended to mean at least one acid.

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%).

The term "comprising" (and its grammatical variations) as used herein is used in the inclusive sense of "having" or "including" and not in the exclusive sense of "consisting only of".

"Keratinous substrates" or variations thereof as used herein, includes skin and keratin fibers, "Keratin fiber" as used herein, includes, but is not limited to hair, such as hair on the human head and eyelashes.

As used herein, the term "carbonated" or "carbonation" is understood to mean the combination of a bicarbonate compound and at least one acid.

"Film former" or "film forming polymer" as used herein means a polymer or resin that leaves a film on the substrate to which it is applied, for example, after a solvent accompanying the film former has evaporated, absorbed into and/or dissipated on the substrate. These terms may also refer to a polymer capable, by itself or in the presence of an auxiliary film forming polymer, of forming a continuous or a discontinuous film that adheres to a support and especially to keratin substrates such as keratin fibers or hair.

"Film former" or "film forming polymer" as used herein may also be referred to as fixing polymers when such polymers are employed to fix or keep keratin fibers in a particular configuration or shape or arrangement.

Among the film forming polymers that may be used in the cosmetic composition as disclosed herein, non-limiting mention may be made of cationic polymers, anionic polymers, nonionic polymers, amphoteric polymers, silicone polymers, or mixtures thereof.

The term "aqueous composition" or variations thereof means that the composition comprises water and optionally, substances of a formulation which, due to their hydrophilic character, can be mixed and/or dissolved and/or dispersed in water.

"Volatile", as used herein, means having a flash point of less than about 100° C.

"Non-volatile", as used herein, means having a flash point of greater than about 100° C.

"Substituted" as used herein, means comprising at least one substituent. Non-limiting examples of substituents include atoms, such as oxygen atoms and nitrogen atoms, as well as functional groups, such as acyloxyalky groups, carboxylic acid groups, amine or amino groups, acylamino groups, amide groups, halogen containing groups, ester groups, thiol groups, sulphonate groups, thiosulphate groups, siloxane groups, and polysiloxane groups. The substituent(s) may be further substituted.

The terms "organic compound" and "having an organic structure" mean compounds containing carbon atoms and hydrogen atoms and optionally heteroatoms such as S, O, N or P, alone or in combination.

As used herein, the terms "applying a composition onto keratin fibers" and "applying a composition onto hair" and variations of these phrases are intended to mean contacting the fibers or hair, with at least one of the compositions of the invention, in any manner.

As used herein, "formed from," means obtained from chemical reaction of, wherein "chemical reaction," includes spontaneous chemical reactions and induced chemical reactions. As used herein, the phrase "formed from," is open ended and does not limit the components of the composition to those listed.

The term "stable" as used herein means that the composition does not exhibit phase separation and/or crystallization.

The term "treat" (and its grammatical variations) as used herein refers to the application of the compositions of the present invention onto keratin fibers such as hair.

The term "shaping" (and its grammatical variations) as used herein includes styling or placing a keratin fiber such as hair, in a particular arrangement, form or configuration; or altering the curvature of a keratinous fiber or other substrate; or re-positioning a keratinous fiber or other substrate to a different arrangement, form or configuration.

As used herein, the terms "method of shaping keratin fibers" or "method of shaping hair" is understood to mean any method for modifying the appearance of the keratin fibers or the hair with respect to their spatial arrangement or configuration or curvature or form. When the keratin fibers comprise hair on the human head, the term "method of shaping keratin fibers" or "method of shaping hair" is also understood to mean any method for curling or waving or embossing the hair or smoothing or straightening the hair, or spiking the hair.

The compositions and methods of the present invention can comprise, consist of, or consist essentially of the essential elements and limitations of the invention described herein, as well as any additional or optional ingredients, components, or limitations described herein or otherwise useful.

Unless otherwise specified herein, all percentages and ratios of components are by weight relative to the total weight of the final composition.

In an embodiment, the present invention relates to a composition, comprising:
  a) at least one bicarbonate compound;
  b) at least one acid;
  c) at least one film forming polymer; and
  d) at least one cosmetically acceptable carrier;
wherein the weight ratio of the at least one bicarbonate compound (a) to the at least one acid (b) is greater than or equal to about 1:1.

In certain embodiments, the above described composition further comprises at least one auxiliary ingredient selected from at least one propellant, at least one emulsifier, at least one rheology modifier, and mixtures thereof.

In another embodiment, the invention relates to an aqueous hair gel cosmetic composition comprising:
  a) sodium bicarbonate;
  b) at least one acid selected from citric acid, lactic acid, and mixtures thereof;
  c) at least one film forming polymer;
  d) a cosmetically acceptable carrier selected from water and water/organic solvent mixture;
  e) at least one emulsifier; and
  f) at least one rheology modifier;
wherein the weight ratio of the at least one bicarbonate (a) to the at least one acid (b) ranges from greater than about 1:1 to about 2:1.

In another embodiment, the invention relates to a hair mousse cosmetic composition comprising:
  a) sodium bicarbonate;
  b) at least one acid selected from citric acid, lactic acid, and mixtures thereof;
  c) at least one film forming polymer;

d) a cosmetically acceptable carrier selected from water and water/organic solvent mixture;
e) at least one propellant;
f) optionally, at least one emulsifier; and
g) optionally, at least one rheology modifier;

wherein the weight ratio of the at least one bicarbonate (a) to the at least one acid (b) ranges from about 2:1 to about 3:1.

In an embodiment, the at least one acid in any one of the above-described compositions is selected from citric acid, lactic acid, and mixtures thereof.

In one embodiment, the film forming polymer in any one of the above-described compositions is an anionic polymer. In a particular embodiment the anionic film forming polymer is Polyacrylate-2 Crosspolymer.

In another particular embodiment the anionic film forming polymer is Polyacrylate-32 Crosspolymer.

In another embodiment, the anionic film forming polymer in any one of the above-described compositions is a silicone copolymer. In a particular embodiment, the silicone copolymer is Crotonic Acid/Vinyl C8-12 Isoalkyl Esters/Va/Bis-Vinyldimethicone Crosspolymer.

In another embodiment, the film forming polymer in any one of the above-described compositions comprises Crotonic Acid/Vinyl C8-12 lsoalkyl Esters/Va/Bis-Vinyldimethicone Crosspolymer and a second film forming polymer chosen from Polyacrylate-2 Crosspolymer, Polyacrylate-32 Crosspolymer, and mixtures thereof.

In other embodiments, the anionic film forming polymer comprises Polyacrylate-2 Crosspolymer and Polyacrylate-32 Crosspolymer.

In other embodiments, the film forming polymer in any one of the above-described compositions is chosen from sodium polystyrene sulfonate, carbomer, VP/VA Copolymer, polyquaternium-11, Octylacrylamide/Acrylates/Butylaminoethyl Methacrylate Copolymer, and mixtures thereof.

In an embodiment, the invention relates to a cosmetic composition comprising:
a) from about 0.5% to about 2% by weight of sodium bicarbonate;
b) from about 0.25% to about 1% by weight at least one acid selected from citric acid, lactic acid, and mixtures thereof;
c) from about 0.5% to about 8% by weight at least one film forming polymer;
d) a cosmetically acceptable carrier selected from water and water/organic solvent mixture;
e) optionally, at least one propellant;
f) optionally, at least one emulsifier;
g) optionally, at least one rheology modifier; and
h) optionally, at least one neutralizing agent;

wherein the weight ratio of the at least one bicarbonate (a) to the at least one acid (b) ranges from greater than about 1:1 to about 3:1; and
wherein all weights are relative to the total weight of the composition.

In an embodiment, the present invention relates to a method of making up or enhancing the appearance of keratin fibers, in particular hair, involving applying onto the keratin fibers, any one of the above described cosmetic compositions of the present invention.

In an embodiment, the present invention relates to a method of styling or shaping hair, involving applying onto the hair, any one of the above described cosmetic compositions of the present invention.

The compositions according to various exemplary embodiments of the present invention may also impart improved and/or increased ease of styling or shaping hair. The improved ease of styling or shaping hair may be facilitated by the decreased drying time of the compositions of the present invention on the hair.

As such, the present disclosure also relates to methods of improving or increasing the ease of styling the hair and decreasing or controlling frizziness of hair using the compositions of the present invention.

Another embodiment of the invention relates to a method of making a cosmetic composition comprising combining:
a) at least one bicarbonate compound;
b) at least one acid;
c) at least one film forming polymer;
d) at least one cosmetically acceptable carrier;
e) optionally, at least one propellant;
f) optionally, at least one emulsifier; and
g) optionally, at least one rheology modifier wherein the weight ratio of the at least one bicarbonate compound (a) to the at least one acid (b) is greater than or equal to about 1:1.

The present invention also relates to a method of styling or shaping hair comprising (a) providing any one of the above-described compositions of the present invention, and (b) providing instructions on applying said composition to hair.

It should be understood that the precise numerical values used in the specification, including the examples and claims, form additional embodiments of the invention, and are intended to include any ranges which can be narrowed to any to end points disclosed within the exemplary ranges and values provided. Efforts have been made to ensure the accuracy of the numerical values disclosed. However, any measured value can inherently contain certain errors resulting from the standard deviation found in its respective measuring technique.

Bicarbonate Compound

The at least one bicarbonate compound of the present invention may be chosen from alkali metal or alkaline-earth metal bicarbonate compounds, The bicarbonate compound is chosen for its reactivity with regard to the associated at least one acid of the present invention. Its choice clearly falls within the competence of a person skilled in the art.

Among the examples of bicarbonate compounds that may be used in the context of the present invention, mention may be made especially of sodium bicarbonate, potassium bicarbonate, magnesium bicarbonate, calcium bicarbonate, and mixtures thereof.

Sodium bicarbonate is most particularly suitable for use in the invention.

The amount of the at least one bicarbonate compound of the present invention can be adjusted with regard to that of the associated at least one acid of the present invention. It may especially range from about 0.25% to about 9% by weight, preferably from about 0.5% to about 5% by weight, more preferably from about 0.5% to about 4% by weight, even more preferably from about 0.5% to about 2% by weight, relative to the total weight of the composition, including all ranges and subranges therebetween.

In some embodiments, the amount of the at least one bicarbonate compound of the present invention is at about 0.5% by weight, or at about 1% by weight, or at about 1.4% by weight, or at about 1.5% by weight, or at about 1.88% by weight, or at about 2% by weight, relative to the total weight of the composition.

Acid

The at least one acid compound of the present invention may be chosen from mineral or organic acids such as hydrochloric acid, orthophosphoric acid, sulfuric acid, sulfonic acids, and carboxylic acids, for instance acetic acid, tartaric acid, citric acid, lactic acid, and mixtures thereof.

The at least one acid of the present invention is preferably chosen from citric acid, lactic acid, and mixtures thereof.

In certain embodiments of the present invention, the at least one acid is citric acid.

In other embodiments of the present invention, the at least one acid is lactic acid.

The amounts of the at least one acid in the compositions of the present invention may range from about 0.25% to about 3% by weight, preferably from about 0.25% to about 2% by weight, more preferably from about 0.25% to about 1% by weight, relative to the total weight of the composition, including all ranges and subranges therebetween.

In some embodiments, the amount of the at least one acid in the compositions of the present invention is at about 0.25% by weight, or at about 0.3% by weight, or at about 0.47% by weight, or at about 0.5% by weight, or at about 0.6% by weight, or at about 0.94% by weight, or at about 1% by weight, or at about 2% by weight, relative to the total weight of the composition.

The amounts of the at least one bicarbonate compound may be adjusted according to the amounts of the at least one acid in the compositions of the present invention in terms of weight ratios of the at least one bicarbonate compound to the at least one acid.

In certain embodiments, the weight ratio of the at least one bicarbonate compound to the at least one acid is greater than or equal to about 1:1.

In other embodiments, the weight ratio of the at least one bicarbonate compound to the at least one acid is from about 1:1 to about 3:1, or such as from about 1.5:1 to about 3:1, or such as from about 2:1 to about 3:1, including all ranges and subranges there between.

In some embodiments, the weight ratio of the at least one bicarbonate compound to the at least one acid is at about 1:1, or is greater than about 1:1, such as at about 1.5:1, or at about 2:1, or at about 3:1.

In certain embodiments, the weight ratio of the at least one bicarbonate compound to the at least one acid is greater than about 1:1.

Without wishing to be bound to any one theory, it is believed that the combination of the at least one acid and the at least one bicarbonate compound (carbonated system) with the at least one film forming polymer alters the film forming properties of the polymer such that the resulting composition imparts significantly better styling and shaping hold properties to keratin fibers while providing a clean, natural, and no tacky feel to the fibers as compared to conventional compositions that do not contain the carbonated system.

Film Forming Polymers

The film forming polymer of the present invention is chosen from anionic, cationic, amphoteric and nonionic film forming polymers and mixtures thereof. The anionic film forming polymers generally used are polymers containing groups derived from carboxylic, sulfonic or phosphoric acid, and have a number-average molecular mass of between approximately 500 and 5 000 000.

The anionic film forming polymers containing carboxylic groups are:

A) copolymers of acrylic acid and of acrylamide sold in the form of their sodium salts, for example, the sodium salts of polyhydroxycarboxylic acids;

B) copolymers of acrylic or methacrylic acid with a monoethylenic monomer such as ethylene, styrene, vinyl esters, acrylic or methacrylic acid esters, optionally grafted onto a polyalkylene glycol such as polyethylene glycol and optionally crosslinked. Such polymers are described in particular in French patent No. 1 222 944 and German patent application No. 2 330 956, the copolymers of this type comprising an optionally N-alkylated and/or hydroxyalkylated acrylamide unit in their chain. Mention may also be made of the acrylic acid/ethyl acrylate/N-tert-butylacrylamide terpolymers. Mention may also be made of copolymers of acrylic acid and of $C_1$-$C_4$ alkyl methacrylate and terpolymers of vinylpyrrolidone, of acrylic acid and of $C_1$-$C_{20}$ alkyl methacrylate, for example of lauryl, and methacrylic acid/ethyl acrylate/tert-butyl acrylate terpolymers.

Mention may also be made of methacrylic acid/acrylic acid/ethyl acrylate/methyl methacrylate copolymers as an aqueous dispersion;

C) crotonic acid copolymers, such as those comprising vinyl acetate or propionate units in their chain and optionally other monomers such as allyl esters or methallyl esters, vinyl ether or vinyl ester of a linear or branched saturated carboxylic acid with a long hydrocarbon-based chain, such as those containing at least 5 carbon atoms, it being possible for these polymers optionally to be grafted or crosslinked, or alternatively another vinyl, allyl or methallyl ester monomer of an α- or β-cyclic carboxylic acid. Polymers of these kinds are described in references including French patents Nos. 1 222 944, 1 580 545, 2 265 782, 2 265 781, 1 564 110 and 2 439 798. Commercial products that come under this category are the resins 28-29-30, 26-13-14 and 28-13-10 sold by National Starch;

D) copolymers of monounsaturated $C_4$-$C_8$ carboxylic acids or anhydrides, chosen from:

copolymers comprising (i) one or more maleic, fumaric or itaconic acids or anhydrides and (ii) at least one monomer chosen from vinyl esters, vinyl ethers, vinyl halides, phenylvinyl derivatives, acrylic acid and its esters, the anhydride functions of these copolymers being optionally monoesterified or monoamidated. Polymers of these kinds are described more particularly in U.S. Pat. Nos. 2,047,398, 2,723,248, 2,102,113 and in GB patent No. 839 805. Commercial products are especially those sold under the names Gantrez® AN or ES;

copolymers comprising (i) one or more maleic, citraconic or itaconic anhydride units and (ii) one or more monomers chosen from allyl or methallyl esters optionally comprising one or more acrylamide, methacrylamide, α-olefin, acrylic or methacrylic ester, acrylic or methacrylic acid or vinylpyrrolidone groups in their chain, the anhydride functions of these copolymers optionally being monoesterified or monoamidated.

These polymers are described, for example, in French patents Nos. 2 350 384 and 2 357 241 by the Applicant.

E) Polyacrylamides containing carboxylate groups.

F) Homopolymers and copolymers comprising sulfonic groups, such as the polymers containing vinylsulfonic, styrenesulfonic, naphthalenesulfonic or acrylamidoalkylsulfonic units. These polymers may in particular be chosen from:

polyvinylsulfonic acid salts having a molecular weight of approximately between 1000 and 100 000, and also the copolymers with an unsaturated comonomer such as acrylic or methacrylic acids and esters thereof, and also acrylamide or derivatives thereof, vinyl ethers and vinylpyrrolidone;

polystyrenesulfonic acid salts such as the sodium salts. These compounds are described in patent FR 2 198 719;

polyacrylamidesulfonic acid salts, such as those mentioned in patent U.S. Pat. No. 4,128,631 and more particularly polyacrylamidoethylpropanesulfonic acid.

As another anionic film forming polymer that can be used according to the invention, mention may be made of the branched block anionic polymer sold under the name FIXATE G-100 L by the company Lubrizol.

Other anionic film forming polymers that may be used are chosen from copolymers of acrylic acid or of acrylic esters, such as acrylic acid/ethyl acrylate/N-tert-butylacrylamide terpolymers, copolymers derived from crotonic acid, such as vinyl acetate/vinyl tert-butylbenzoate/crotonic acid terpolymers and crotonic acid/vinyl acetate/vinyl neododecanoate terpolymers, polymers derived from maleic, fumaric or itaconic acids or anhydrides with vinyl esters, vinyl ethers, vinyl halides, phenylvinyl derivatives and acrylic acid and esters thereof, such as the methyl vinyl ether/monoesterified maleic anhydride copolymers, the copolymers of methacrylic acid and of methyl methacrylate, copolymers of methacrylic acid and of ethyl acrylate, vinyl acetate/crotonic acid copolymers, vinyl acetate/crotonic acid copolymers grafted with polyethylene glycol, and mixtures thereof.

Other anionic film forming polymers the may be used includes a silicone copolymer compound such as a silicone polyvinyl acetate compound.

The silicone copolymer compound may be chosen from a cross-linked anionic copolymer comprised of organic polymer blocks and silicone blocks, resulting in a multiblock polymer structure.

In particular, the silicone copolymer compound of the present disclosure may be chosen from cross-linked anionic copolymers comprising at least one cross-linked polysiloxane structural unit. Examples of these polymers have been described in the PCT publication, WO2011069786, published Jun. 16, 2011.

According to the invention, the anionic film forming polymers are preferably chosen from copolymers of acrylic and methacrylic acid or their salts, crotonic acid copolymers, copolymers of monounsaturated C4-C8 carboxylic acids or anhydrides, polyacrylamides comprising carboxylate groups, homopolymers or copolymers comprising sulfonic groups, anionic polyurethanes, anionic silicone copolymer compounds, sulfopolyesters, and mixtures thereof.

In preferred embodiments, the anionic film forming polymer is Polyacrylate-2 Crosspolymer, known by the tradename of FIXATE SUPERHOLD POLYMER, commercially available from Lubrizol.

In other preferred embodiments, the anionic film forming polymer is Polyacrylate-32 Crosspolymer, known by the tradename of FIXATE DESIGN POLYMER, commercially available from Lubrizol.

In other preferred embodiments, the anionic film forming polymer is a silicone copolymer compound, known by the INCI name Crotonic Acid/Vinyl C8-12 Isoalkyl Esters/Va/Bis-Vinyldimethicone Crosspolymer, which is a copolymer of Crotonic Acid, vinyl C8-12 isoalkyl esters and Vinyl Acetate crosslinked with bis-vinyldimethicone. This compound is commercially available from the company Wacker Chemie AG under the tradename Wacker Belsil® P1101 (may also be known under the tradename Wacker Belsil® P101). Crotonic Acid/Vinyl C8-12 Isoalkyl Esters/VA/Bis-Vinyldimethicone Crosspolymer is also known by the technical name of Crotonic Acid/Vinyl C8-12 Isoalkyl Esters/VA/divinyldimethicone Crosspolymer.

In some embodiments, the anionic film forming polymer is sodium polystyrene sulfonate, known by the tradename of FLEXAN II, commercially available from Azko Nobel.

In yet other embodiments, the anionic film forming polymer is of the acrylic type, and known under the tradename of CARBOPOL and commercially available from Lubrizol, such as the film former known by the INCI name carbomer.

The cationic film forming polymers that can be used according to the present invention are preferably chosen from polymers comprising primary, secondary, tertiary and/or quaternary amine groups forming part of the polymer chain or directly attached thereto, and having a molecular weight of between 500 and approximately 5 000 000 and preferably between 1000 and 3 000 000.

Among these polymers, mention may be made more particularly of the following cationic polymers:
(1) homopolymers or copolymers derived from acrylic or methacrylic esters or amides and comprising at least one of the units of the following formulae:

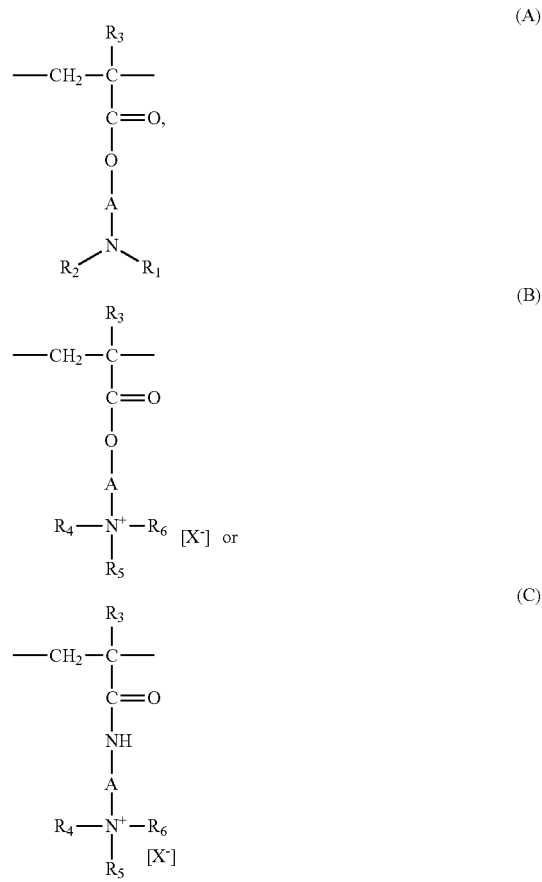

in which:
$R_3$ denotes a hydrogen atom or a $CH_3$ radical;
A is a linear or branched alkyl group comprising from 1 to 6 carbon atoms or a hydroxyalkyl group comprising from 1 to 4 carbon atoms;
$R_4$, $R_5$ and $R_6$, which may be identical or different, represent an alkyl group containing from 1 to 18 carbon atoms or a benzyl radical;
$R_1$ and $R_2$, which are identical or different, each represent a hydrogen atom or an alkyl group having from 1 to 6 carbon atoms;
X denotes a methosulfate anion or a halide such as chloride or bromide.

The copolymers of the family (1) also contain one or more units derived from comonomers that may be chosen from the family of acrylamides, methacrylamides, diacetone acrylamides, acrylamides and methacrylamides substituted on the nitrogen with lower ($C_1$-$C_4$) alkyl groups, groups derived from acrylic or methacrylic acids or esters thereof, vinyl-lactams such as vinylpyrrolidone or vinylcaprolactam, and vinyl esters.

Thus, among these copolymers of family (1), mention may be made of:

copolymers of acrylamide and of dimethylaminoethyl methacrylate quaternized with dimethyl sulfate or with a dimethyl halide, such as the product sold under the name Hercofloc® by the company Hercules, copolymers of acrylamide and of methacryloyloxyethyltrimethylammonium chloride, described, for example, in patent application EP-A-080 976, the copolymer of acrylamide and of methacryloyloxyethyltrimethylammonium methosulfate, quaternized or non-quaternized vinylpyrrolidone/dialkylaminoalkyl acrylate or methacrylate copolymers, polymers containing a vinylpyrrolidone unit, dimethylaminoethyl methacrylate/vinylcaprolactam/vinylpyrrolidone terpolymers, and quaternized vinylpyrrolidone/dimethylaminopropylmethacrylamide copolymers;

(2) non-cellulosic cationic polysaccharides, preferably containing quaternary ammonium, such as those described in U.S. Pat. Nos. 3,589,578 and 4,031,307, such as guar gums containing trialkylammonium cationic groups;

(3) quaternary copolymers of vinylpyrrolidone and of vinylimidazole;

(4) chitosans or salts thereof; the salts that can be used are, in particular, chitosan acetate, lactate, glutamate, gluconate or pyrrolidonecarboxylate;

(5) cationic cellulose derivatives such as copolymers of cellulose or of cellulose derivatives grafted with a water-soluble monomer comprising a quaternary ammonium, and described in particular in U.S. Pat. No. 4,131,576, such as hydroxyalkylcelluloses, for instance hydroxymethyl-, hydroxyethyl- or hydroxypropylcelluloses grafted in particular with a methacryloyloxyethyltrimethylammonium, methacrylamidopropyltrimethylammonium or dimethyldiallylammonium salt.

The amphoteric film forming polymers that may be used in accordance with the invention may be selected from polymers comprising units B and C distributed randomly in the polymeric chain, where B denotes a unit deriving from a monomer containing at least one basic nitrogen atom, and C denotes a unit deriving from an acidic monomer containing one or more carboxylic or sulfonic groups, or else B and C may denote groups deriving from zwitterionic carboxybetaine or sulfobetaine monomers;

B and C may also denote a cationic polymer chain comprising primary, secondary, tertiary or quaternary amine groups, in which at least one of the amine groups carries a carboxylic or sulfonic group connected via a hydrocarbon group, or else B and C form part of a chain of a polymer with an apdicarboxylic ethylene unit, in which one of the carboxyl groups has been reacted with a polyamine containing one or more primary or secondary amine groups.

The amphoteric film forming polymers corresponding to the definition given above that are more particularly preferred are chosen from the following polymers:

(1) copolymers containing acidic vinyl units and basic vinyl units, such as those resulting from the copolymerization of a monomer derived from a vinyl compound bearing a carboxylic group such as, more particularly, acrylic acid, methacrylic acid, maleic acid, α-chloroacrylic acid, and of a basic monomer derived from a substituted vinyl compound containing at least one basic atom, such as, more particularly, dialkylaminoalkyl methacrylate and acrylate, dialkylaminoalkylmethacrylamide and acrylamide. Such compounds are described in U.S. Pat. No. 3,836,537;

(2) polymers comprising units derived from:
  a) at least one monomer chosen from acrylamides or methacrylamides substituted on the nitrogen atom with an alkyl group,
  b) at least one acidic comonomer containing one or more reactive carboxylic groups, and
  c) at least one basic comonomer such as esters containing primary, secondary, tertiary and quaternary amine substituents of acrylic and methacrylic acids and the product of quaternization of dimethylaminoethyl methacrylate with dimethyl or diethyl sulfate.

The N-substituted acrylamides or methacrylamides that are more particularly preferred according to the invention are compounds in which the alkyl groups contain from 2 to 12 carbon atoms and more particularly N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers are chosen more particularly from acrylic, methacrylic, crotonic, itaconic, maleic and fumaric acids and also from monoalkyl esters, having 1 to 4 carbon atoms, of the maleic or fumaric acids or anhydrides.

The preferred basic comonomers are aminoethyl, butylaminoethyl, N,N'-dimethylaminoethyl and N-tert-butylaminoethyl methacrylates.

The copolymers whose INCI name is octylacrylamide/acrylates/butylaminoethyl methacrylate copolymer, such as the products sold under the name Amphomer® by the company Akzo Nobel, are particularly used.

(3) Crosslinked and acylated polyaminoamides partially or totally derived from polyaminoamides of general formula:

(IX)

in which $R_{10}$ represents a divalent group derived from a saturated dicarboxylic acid, from an aliphatic mono- or dicarboxylic acid with an ethylenic double bond, from an ester of a lower alkanol having 1 to 6 carbon atoms with these acids, or from a group deriving from the addition of any of said acids with a bis-primary or bis-secondary amine, and Z denotes a group deriving from a bis-primary or mono- or bis-secondary polyalkylene-polyamine, and preferably represents:

a) in proportions of from 60 mol % to 100 mol %, the group

(X)

where x=2 and p=2 or 3, or alternatively x=3 and p=2, this group deriving from diethylenetriamine, from triethylenetetraamine or from dipropylenetriamine;

b) in proportions of from 0 to 40 mol %, the group (X) above in which x=2 and p=1 and which is derived from ethylenediamine, or the group derived from piperazine:

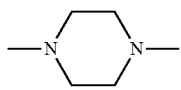

c) in proportions of from 0 to 20 mol %, the —NH—$(CH_2)_6$—NH— group being derived from hexamethylenediamine, these polyaminoamides being crosslinked by addition reaction of a difunctional crosslinking agent chosen from epihalohydrins, diepoxides, dianhydrides and bis-unsaturated derivatives, using from 0.025 to 0.35 mol of crosslinking agent per amine group of the polyaminoamide and acylated by the action of acrylic acid, chloroacetic acid or an alkane sultone, or salts thereof.

The saturated carboxylic acids are preferably chosen from acids having 6 to 10 carbon atoms, such as adipic acid, 2,2,4-trimethyladipic acid and 2,4,4-trimethyladipic acid, terephthalic acid, acids containing an ethylenic double bond such as, for example, acrylic acid, methacrylic acid and itaconic acid.

The alkane sultones used in the acylation are preferably propane sultone or butane sultone; the salts of the acylating agents are preferably the sodium or potassium salts;

(4) polymers comprising zwitterionic units of formula:

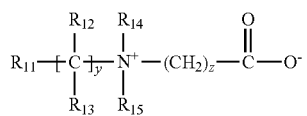

(XI)

in which $R_{11}$ denotes a polymerizable unsaturated group such as an acrylate, methacrylate, acrylamide or methacrylamide group, y and z represent an integer from 1 to 3, $R_{12}$ and $R_{13}$ represent a hydrogen atom or a methyl, ethyl or propyl group, $R_{14}$ and $R_{15}$ represent a hydrogen atom or an alkyl group such that the sum of the carbon atoms in $R_{14}$ and $R_{15}$ does not exceed 10.

The polymers comprising such units may also comprise units derived from non-zwitterionic monomers such as dimethyl- or diethylaminoethyl acrylate or methacrylate or from alkyl acrylates or methacrylates, from acrylamides or methacrylamides, or vinyl acetate.

By way of example, mention may be made of the methyl methacrylate/methyl dimethylcarboxymethylammonioethyl methacrylate copolymers.

(5) polymers derived from chitosan comprising monomer units corresponding to the following formulae:

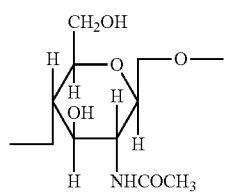

(D)

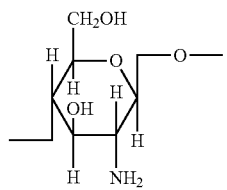

(E)

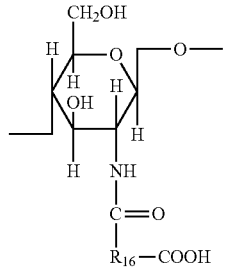

(F)

the unit (D) being present in proportions of between 0 and 30%, the unit (E) in proportions of between 5% and 50% and the unit (F) in proportions of between 30% and 90%, it being understood that, in this unit (F), $R_{16}$ represents a group of formula:

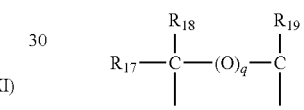

in which, if q=0, $R_{17}$, $R_{18}$ and $R_{19}$, which may be identical or different, each represent a hydrogen atom, a methyl, hydroxyl, acetoxy or amino residue, a monoalkylamine residue or a dialkylamine residue that are optionally interrupted by one or more nitrogen atoms and/or optionally substituted with one or more amine, hydroxyl, carboxyl, alkylthio or sulfonic groups, an alkylthio residue in which the alkyl group bears an amino residue, at least one of the groups $R_{17}$, $R_{18}$ and $R_{19}$ being, in this case, a hydrogen atom;

or if q=1, $R_{17}$, $R_{18}$ and $R_{19}$ each represent a hydrogen atom, and also the salts formed by these compounds with bases or acids.

(6) Polymers with units corresponding to the general formula (XII) are described, for example, in French patent 1 400 366:

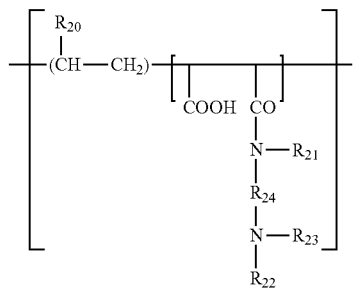

(XII)

in which $R_{20}$ represents a hydrogen atom or a $CH_3O$, $CH_3CH_2O$ or phenyl group, $R_{21}$ denotes a hydrogen atom or a lower alkyl group such as methyl or ethyl, $R_{22}$ denotes a hydrogen atom or a $C_1$-$C_6$ lower alkyl group such as methyl or ethyl, $R_{23}$ denotes a lower $C_1$-$C_6$ alkyl group such as methyl or ethyl, or a group corresponding to the following formula: —$R_{24}$—N($R_{22}$)$_2$, $R_{24}$ representing a —CH$_2$—CH$_2$—, —CH$_2$—CH$_2$—CH$_2$— or —CH$_2$—CH(CH$_3$)— group, $R_{22}$ having the meanings mentioned above.

(7) Polymers derived from the N-carboxyalkylation of chitosan, such as N-carboxymethylchitosan or N-carboxybutylchitosan.

(8) Amphoteric polymers of the -D-X-D-X type chosen from:
  a) polymers obtained by the action of chloroacetic acid or sodium chloroacetate on compounds comprising at least one unit of formula:

-D-X-D-X-D- (XIII)

where D denotes a group

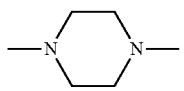

and X denotes the symbol E or E', E or E', which may be identical or different, denote a divalent group that is an alkylene group with a straight or branched chain containing up to 7 carbon atoms in the main chain, which is unsubstituted or substituted with hydroxyl groups and which can comprise, in addition to the oxygen, nitrogen and sulfur atoms, 1 to 3 aromatic and/or heterocyclic rings; the oxygen, nitrogen and sulfur atoms being present in the form of ether, thioether, sulfoxide, sulfone, sulfonium, alkylamine or alkenylamine groups, hydroxyl, benzylamine, amine oxide, quaternary ammonium, amide, imide, alcohol, ester and/or urethane groups.

b) The polymers of formula:

-D-X-D-X— (XIV)

where D denotes a group

and X denotes the symbol E or E' and at least once E'; E having the meaning given above and E' is a divalent group that is an alkylene group with a straight or branched chain having up to 7 carbon atoms in the main chain, which is unsubstituted or substituted with one or more hydroxyl groups and containing one or more nitrogen atoms, the nitrogen atom being substituted with an alkyl chain that is optionally interrupted by an oxygen atom and necessarily comprising one or more carboxyl functions or one or more hydroxyl functions and betainized by reaction with chloroacetic acid or sodium chloroacetate.

(9) ($C_1$-$C_5$)alkyl vinyl ether/maleic anhydride copolymers partially modified by semiamidation with an N,N-dialkylaminoalkylamine such as N,N-dimethylaminopropylamine or by semiesterification with an N,N-dialkylaminoalkanol. These copolymers can also comprise other vinyl comonomers such as vinylcaprolactam.

Among the amphoteric film forming polymers mentioned above, the ones that are most particularly preferred according to the invention are those of family (3), such as the copolymers whose INCI name is octylacrylamide/acrylates/butylaminoethyl methacrylate copolymer, such as the products sold under the names Amphomer®, by the company Akzo Nobel.

The nonionic film forming polymers that may be used according to the present invention are chosen, for example, from:
  polyalkyloxazolines;
  vinyl acetate homopolymers;
  vinyl acetate copolymers, for instance copolymers of vinyl acetate and of acrylic ester, copolymers of vinyl acetate and of ethylene, or copolymers of vinyl acetate and of maleic ester, for example of dibutyl maleate;
  homopolymers and copolymers of acrylic esters, such as for example, copolymers of alkyl acrylates and alkyl methacrylates2;
  copolymers of acrylonitrile and a nonionic monomer, chosen, for example, from butadiene and alkyl (meth)acrylates;
  styrene homopolymers;
  styrene copolymers, for instance copolymers of styrene and of an alkyl (meth)acrylate; copolymers of styrene, of alkyl methacrylate and of alkyl acrylate; copolymers of styrene and of butadiene; or copolymers of styrene, of butadiene and of vinylpyridine;
  polyamides;
  vinyllactam homopolymers such as vinylpyrrolidone homopolymers, and such as polyvinylcaprolactam; and
  vinyllactam copolymers such as a poly(vinylpyrrolidone/vinyllactam) copolymer, poly(vinylpyrrolidone/vinyl acetate) copolymers; and poly(vinylpyrrolidone/vinyl acetate/vinyl propionate) terpolymers.

The alkyl groups of the abovementioned nonionic polymers preferably have from 1 to 6 carbon atoms.

According to the invention, it is also possible to use film forming polymers of grafted silicone type comprising a polysiloxane portion and a portion constituted of a non-silicone organic chain, one of the two portions constituting the main chain of the polymer and the other being grafted to the said main chain.

These polymers are described, for example, in patent applications EP-A-0 412 704, EP-A-0 412 707, EP-A-0 640 105 and WO 95/00578, EP-A-0 582 152 and WO 93/23009 and U.S. Pat. Nos. 4,693,935, 4,728,571 and 4,972,037.

These polymers may be amphoteric, anionic or nonionic, and are preferably anionic or nonionic.

Polymers of these kinds are, for example, the copolymers obtainable by radical polymerization from the mixture of monomers formed by:
  a) from 50% to 90% by weight of tert-butyl acrylate,
  b) from 0% to 40% by weight of acrylic acid,
  c) from 5% to 40% by weight of a silicone macromer of formula:

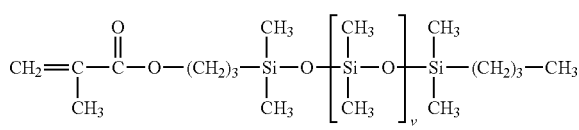

in which v is a number ranging from 5 to 700, the weight percentages being calculated relative to the total weight of the monomers.

Other examples of grafted silicone polymers are in particular polydimethylsiloxanes (PDMSs) to which mixed polymer units of the poly(meth)acrylic acid type and of the poly(alkyl (meth)acrylate) type are grafted via a thiopropylene-type connecting link and polydimethylsiloxanes (PDMSs) to which polymer units of the poly(isobutyl (meth) acrylate) type are grafted via a thiopropylene-type connecting link.

As film forming polymers it is also possible to use functionalized or non-functionalized, cationic, nonionic, anionic or amphoteric, silicone or non-silicone polyurethanes, or mixtures thereof.

The polyurethanes to which the present invention is particularly directed are those described in patent applications EP 0 751 162, EP 0 637 600, EP 0 648 485 and FR 2 743 297, of which the Applicant is the proprietor, and also in patent applications EP 0 656 021 and WO 94/03510 from the company BASF, and EP 0 619 111 from the company National Starch.

In one embodiment, the film forming polymer or polymers used in the composition according to the invention is or are film forming polymers comprising at least one vinyl-lactam unit.

The film forming polymer or polymers used in the composition according to the invention preferably is or are nonionic film forming polymers, more particularly nonionic film forming polymers chosen from vinyllactam homopolymers, such as vinylpyrrolidone homopolymers, polyvinylcaprolactam, and vinyllactam copolymers, such as a poly(vinylpyrrolidone/vinyllactam) copolymer, poly(vinylpyrrolidone/vinyl acetate) copolymers, and poly(vinylpyrrolidone/vinyl acetate/vinyl propionate) terpolymers.

More preferentially, the nonionic film forming polymer or polymers used in the composition according to the invention is or are chosen from vinylpyrrolidone homopolymers and poly(vinylpyrrolidone/vinyl acetate) copolymers.

Silicone Resins and Silicone Copolymers

In accordance with other exemplary embodiments, silicone resins and silicone copolymers may also be used as the at least one film forming polymer.

Film forming silicone resins and copolymers are described, for example, in U.S. Pat. No. 7,790,148 (L'Oreal), U.S. Pat. No. 7,094,842 (L'Oreal), US2011/0189, 117 (L'Oreal), US2010/0297050 (L'Oreal), US 2007/0093619 and 2006/0013791, 2005/0201961, all of which are herein incorporated by reference.

Exemplary film forming silicone resins are cross-linked polyorganosiloxane polymers. The nomenclature of silicone resins is known under the name "MDTQ", the resin being described as a function of the various monomeric siloxane units it includes, each of the letters "MDTQ" characterizing one type of unit. Examples of commercially available polymethylsilsesquioxane resins that may be mentioned are those that are sold by the supplier Wacker under the reference Resin MK such as Belsil® PMS MK, and by the supplier SHIN-ETSU under the references KR-220L.

Examples of commercially available polypropylsilsesquioxane resins useful in the invention include those sold under the reference DC®670 by the supplier Dow Corning, and Silform® Flexible Resin from the supplier Momentive.

Examples of a polyphenylsilsesquioxane resins useful in the invention include those available from Wacker.

Siloxysilicate resins that may be used include trimethylsiloxysilicate resins (TMS®) such as those sold under the reference SR1000 by the supplier Momentive Performance Materials or under the reference TMS® 803 by the supplier Wacker. Trimethylsiloxysilicate resins are also available in a solvent such as cyclomethicone, sold under the name "KF-7312J" by the supplier Shin-Etsu, or "DC® 749", "DC® 593" by the supplier Dow Corning.

Pressure-sensitive adhesive silicone copolymers are also herein contemplated. Such copolymers are available, for example from Dow Corning under the reference BIO-PSA and described in U.S. Pat. No. 5,162,410.

Silicone copolymers derived from the reaction of a silicone resin such as those described above and of a diorganosiloxane such as that described in the document WO 2004/073626 are also contemplated.

The amount of film forming polymer or polymers used in the compositions according to the present invention is from about 0.5% to about 10% by weight, preferably from about 0.5% to about 8% by weight, such as from about 0.6% to about 7.625% by weight, or such as from about 0.85% to about 7.625% by weight, or such as at about 7.625% by weight, or at about 6.1% by weight, or at about 3.3% by weight, or at about 3.0% by weight, or at about 2.85% by weight, or at about 2.29% by weight, or at about 1.434% by weight, or at about 1.5% by weight, or at about 1% by weight, or at about 0.85% by weight, or at about 0.6% by weight, with all weights of the film forming polymer being the weight of the active material and relative to the total weight of the composition, including all ranges and subranges therebetween.

In some embodiments, when the film forming polymer is selected from Polyacrylate-2 Crosspolymer, Polyacrylate-32 Crosspolymer, and their mixtures, the amount of film forming polymer or polymers used in the compositions according to the present invention is from about 1.434% to about 7.625% by weight of the active material and relative to the total weight of the composition, including all ranges and subranges therebetween.

In other embodiments, when the compositions of the present invention are in the form of a gel, the amount of film forming polymer or polymers used is preferably from about 3.05% to about 7.625% by weight of the active material and relative to the total weight of the composition, including all ranges and subranges therebetween.

In other embodiments, when the compositions of the present invention are in the form of a mousse, the amount of film forming polymer or polymers used is preferably from about 1.434% to about 2.29% by weight of the active material and relative to the total weight of the composition, including all ranges and subranges therebetween.

In some other embodiments, when the film forming polymer is selected from Crotonic Acid/Vinyl C8-12 Isoalkyl Esters/Va/Bis-Vinyldimethicone Crosspolymer, sodium polystyrene sulfonate, carbomer, VP/VA Copolymer, polyquaternium-11, Octylacrylamide/Acrylates/Butylaminoethyl Methacrylate Copolymer, and mixtures thereof, the amount of film forming polymer or polymers used in the compositions according to the present invention is from about 0.6% to about 3.0% by weight, or such as from about 0.85% to about 1.5% by weight, of the active material and relative to the total weight of the composition, including all ranges and subranges therebetween.

Neutralizing Agent

In preferred embodiments, the at least one film forming polymer of the present invention is neutralized in water or in an aqueous solution with a neutralizing agent. The neutralizing agent of the present invention may added to the water or the aqueous solution before or after or during the time the polymer is added into the cosmetic composition of the present invention.

The neutralizing agent is employed in an amount sufficient to neutralize the polymer of the present invention in water or an aqueous solution. After neutralization, the polymer may be partially or fully neutralized. One indication of neutralization is the clarity of the solution.

Suitable neutralizing agents may be selected from alkali metal carbonates other than bicarbonate compounds, alkali metal phosphates, organic amines, hydroxide base compounds, and mixtures thereof, particularly from ethylamines, ethyleneamines, alkanolamines, cyclic amines and other cyclic compounds, saturated or unsaturated, having one or more nitrogen atoms within the ring.

The organic amines may be chosen from the ones having a pKb at 25° C. of less than 12, such as less than 10 or such as less than 6. It should be noted that this is the pKb corresponding to the function of highest basicity.

Organic amines may be chosen from organic amines comprising one or two primary, secondary, or tertiary amine functions, and at least one linear or branched $C_1$-$C_8$ alkyl groups bearing at least one hydroxyl radical.

Organic amines may also be chosen from alkanolamines such as mono-, di- or trialkanolamines, comprising one to three identical or different $C_1$-$C_4$ hydroxyalkyl radicals, ethylamines, ethyleneamines, quinoline, aniline and cyclic amines, such as pyrroline, pyrrole, pyrrolidine, imidazole, imidazolidine, imidazolidinine, morpholine, pyridine, piperidine, pyrimidine, piperazine, triazine and derivatives thereof.

Among the compounds of the alkanolamine type that may be mentioned include but not limited to: monoethanolamine (also known as monoethanolamine or MEA), diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol, 2-amino-2-methyl-1-propanol, and tris(hydroxymethylamino)methane.

Other examples include but are not limited to: 1,3-diaminopropane, 1,3-diamino-2-propanol, spermine, and spermidine.

In some embodiments, the organic amines are chosen from amino acids.

As non-limiting examples, the amino acids that may be used may be of natural or synthetic origin, in L, D, or racemic form, and comprise at least one acid function chosen from, for instance, carboxylic acid, sulfonic acid, phosphonic acid, and phosphoric acid functions. The amino acids may be in their neutral or ionic form.

Amino acids that may be used in the present disclosure include but are not limited to: aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine, and valine.

Further as non-limiting examples, the amino acids may be chosen from basic amino acids comprising an additional amine function optionally included in a ring or in a ureido function. Such basic amino acids may be chosen from histidine, lysine, arginine, ornithine, and citrulline.

In some embodiments, the organic amines are chosen from organic amines of heterocyclic type. Besides histidine that has already been mentioned in the amino acids, non-limiting mention may also be made of pyridine, piperidine, imidazole, 1,2,4-triazole, tetrazole, and benzimidazole.

In some embodiments, the organic amines are chosen from amino acid dipeptides. Amino acid dipeptides that may be used in the present disclosure include but not limited to: carnosine, anserine, and baleine.

In some embodiments, the organic amines are chosen from compounds comprising a guanidine function. Organic amines of this type that may be used in the present disclosure include, besides arginine that has already been mentioned as an amino acid, creatine, creatinine, 1,1-dimethylguanidine, 1,1-diethylguanidine, glycocyamine, metformin, agmatine, N-amidinoalanine, 3-guanidinopropionic acid, 4-guanidinobutyric acid, and 2-([amino(imino)methyl]amino)ethane-1-sulfonic acid.

The alkali metal phosphates and carbonates that may be used are, for example, sodium phosphate, potassium phosphate, sodium carbonate, sodium bicarbonate, potassium carbonate, potassium bicarbonate, and their derivatives.

The hydroxide base compounds chosen from alkali metal hydroxides, alkaline-earth metal hydroxides, transition metal hydroxides, quaternary ammonium hydroxides, organic hydroxides, and mixtures thereof. Suitable examples are ammonium hydroxide, sodium hydroxide, potassium hydroxide, lithium hydroxide, rubidium hydroxide, caesium hydroxide, francium hydroxide, beryllium hydroxide, magnesium hydroxide, calcium hydroxide, strontium hydroxide, barium hydroxide, molybdenum hydroxide, manganese hydroxide, zinc hydroxide, cobalt hydroxide, cadmium hydroxide, cerium hydroxide, lanthanum hydroxide, actinium hydroxide, thorium hydroxide, aluminium hydroxide, guanidinium hydroxide and mixtures thereof.

According to at least one embodiment, the neutralizing agent is chosen from at least one organic amine such as at least one alkanolamine. Particularly preferred alkanolamines are ethanolamine (also known as monoethanolamine or MEA), triethanolamine, and 2-amino-2-methyl-1-propanol (aminomethyl propanol or AMP), and mixtures thereof. Another particularly preferred alkanolamine is triethanolamine.

In other embodiments, the at least one neutralizing agent is a bicarbonate compound which may be added separately to the film forming polymer during the manufacture of the composition or may be an excess amount from the association of the at least bicarbonate compound with the at least one acid during the preparation of the carbonated system.

The at least one neutralizing agent of the present invention may be employed in an amount of from about 0.01% to about 5% by weight, or such as from about 0.1% to about 3% by weight, or such as from about 0.5% to about 2.5% by weight, based on the total weight of the cosmetic composition of the present invention, including all ranges and subranges therebetween.

In some embodiments, the film forming polymers of the present invention do not have to be neutralized by the at least one neutralizing agent.

In other embodiments, the film forming polymers of the present invention are partially neutralized by the at least one neutralizing agent.

In other embodiments, the film forming polymers of the present invention are fully neutralized by the at least one neutralizing agent.

In some embodiments, when the at least one neutralizing agent is triethanolamine, the amount of neutralizing agent is from about 0.5% to about 2.5% by weight, based on the total weight of the cosmetic composition of the present invention, including all ranges and subranges therebetween.

In some other embodiments, when it is desirable to increase the viscosity of the compositions of the present invention, the at least one neutralizing agent can comprise triethanolamine and aminomethyl propanol.

In yet other embodiments, an excess amount of the at least one bicarbonate compound of the present invention is used to neutralize the film forming polymer and/or achieve a desired pH of the composition of the present invention without requiring high amounts of the at least one neutralizing agent.

Cosmetically Acceptable Carrier

The at least one cosmetically acceptable carrier of the present invention is chosen from water, organic solvents, and mixtures thereof.

The cosmetically acceptable carrier may be composed solely of water, or it may be composed of a mixture of water and at least one organic solvent.

As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, monophenyl ethers of ethylene glycol (phenoxyethanol), propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol.

Other suitable examples of organic solvents are ethylene glycol, propylene glycol, butylene glycol, hexylene glycol, propane diol, glycerin, and mixtures thereof.

The organic solvents for use in the present invention can be volatile or non-volatile compounds.

The cosmetically acceptable carrier of the present invention is typically present in an amount of from about 10% to about 98%, from about 15% to about 95%, or from about 20% to about 90% by weight, based on the total weight of the composition of the present invention, including all ranges and subranges therebetween.

pH

In some embodiments, the pH of the composition of the present invention ranges from about 5 to about 10, or preferably from about 5.5 to about 9, or more preferably from about 6 to about 8, including all ranges and subranges therebetween.

In other embodiments, when the composition of the present invention is in the form of a gel, the pH of the composition of the present invention is from about 6 to about 6.5, including all ranges and subranges therebetween.

In yet other embodiments, when the composition of the present invention is in the form of a mousse, the pH of the composition of the present invention is about 8.

The pH of the composition of the present invention may be adjusted to the desired value using the at least one bicarbonate compound and/or the neutralizing agents of the present invention and/or other conventional acidifying or basifying agents.

All numbers expressing pH values are to be understood as being modified in all instances by the term "about" which encompasses up to +/−3%.

Auxiliary Ingredients

The compositions of the present invention can also comprise auxiliary ingredients, for instance those chosen from the non-exhaustive list such as propellants, emulsifiers, rheology modifiers and film forming agents other than the at least one film forming polymer of the present invention, humectants, conditioning agents, plasticizers, coalescers, fillers, dyes such as oxidative dyes and direct dyes, waxes, surfactants, preserving agents, oils such as mineral, organic or plant oils, fragrances, antioxidants, sunscreens, sequestering agents, softeners, antifoams, basifying agents, wetting agents, spreading agents, dispersants, pigments, proteins, ceramides, vitamins, clays, colloidal minerals, nacreous agents, peptizers, preserving agents, reducing agents, oxidizing agents, pH adjusters, silicones, plant extracts, paraffins, fatty acids, and mixtures thereof.

The person skilled in the art will ensure that any auxiliary ingredient and their amounts are selected in such a way as to cause no detriment to the properties of the compositions disclosed herein.

The at least one auxiliary ingredient may be present in an amount ranging from 0.001% to 50% by weight, relative to the total weight of the entire composition, including all ranges and subranges therebetween.

In certain embodiments, the compositions of the present invention may contain at least one emulsifier.

Emulsifiers or dispersing agents, include, without limitation, any which are compatible with the solvent and ingredients used in the composition of the present invention. The emulsifying agents which can be used according to the invention are those having an HLB of less than 7 and in particular fatty acid esters of polyols such as mono-, di-, tri- or sesqui-oleates or -stearates of sorbitol or glycerol, laurates of glycerol or polethylene glycol; alkyl or alkoxy dimethicone copolyols having an alkyl or alkoxy chain pendent or at the end of a silicone-based backbone having for example from 6 to 22 carbon atoms. The emulsifying agents may also be those having an HLB greater than 7 such as fatty acid esters of polyethylene glycol (monostearate or monolaurate of polyethylene glycol); esters of fatty acids (stearate, oleate) of sorbitol which are polyoxyethylenated; polyoxy ethylenated alkyl (lauryl, cetyl, stearyl, octyl)ethers and dimethicone copolyols. In general, it is possible to use nonionic or anionic or cationic emulsifiers well known to persons skilled in the art.

The nonionic type emulsifiers are fatty acids or amides of polyalkoxylated and/or polyglycerolated fatty acids; polyoxyethylenated and/or polyoxypropylenated fatty alcohols (i.e., compounds prepared by reacting an aliphatic fatty alcohol such as behenyl or cetyl alcohol with ethylene oxide or propylene oxide or an ethylene oxide/propylene oxide mixture); fatty acid esters of polyols, optionally polyoxyethylenated and/or polyoxypropylenated (i.e., compounds prepared by reacting a fatty acid such as stearic acid or oleic acid with a polyol such as, for example, an alkylene glycol or glycerol or a polyglycerol, optionally in the presence of ethylene oxide or propylene oxide or an ethylene oxide/propylene oxide mixture); and polyalkoxylated and/or polyglycerolated alkylphenols; or polyalkoxylated and/or polyglycerolated 1,2- or 1,3-alkanediols; and alkylethers of polyalkoxylated and/or polyglycerolated 1,2- or 1,3-alkanediols or alkenediols, or mixtures thereof.

The esters of fatty acids and polyoxyethylenated polyols for which the polyol is sorbitol are known products (Polysorbate and products sold under the mark "Tween").

The emulsifiers according to the invention can also be anionic surfactants which may have a hydrophilic-lipophilic balance (HLB) ranging from 10 to 40. They are principally salts of fatty acids (for example alkaline salts or organic salts such as amine salts), the said fatty acids having, for example, from 12 to 18 carbon atoms and being able to have a double bond as in the case of oleic acid; the alkaline salts or salts of organic bases of alkyl-sulfuric and alkyl-sulfonic acids having 12 to 18 carbon atoms, of alkyl-arylsulfonic acids whose alkyl chain contains 6 to 16 carbon atoms, the aryl group being, for example, a phenyl group. They are also ether-sulfates, in particular, the sulfatation products of fatty alcohols and polyalkoxylated alkylphenols, in which the aliphatic chain has from 6 to 20 carbon atoms and the polyalkoxylated chain has from 1 to 30 oxyalkylene units, in particular oxyethylene, oxypropylene or oxybutylene. All these anionic surfactants are well known and many among them are commercial products.

The emulsifiers according to the invention can also be cationic surfactants such as quaternary ammonium derivatives.

Particularly preferred emulsifying agents are Isoceteth-20, Polysorbate 20, PEG-40 hydrogenated castor oil, oleth-2, laureth-7, cetyl alcohol, glyceryl stearate, and mixtures thereof.

The emulsifiers may be present in the composition of the present invention in an amount of from 0.05% to 10% by weight, preferably in an amount of from 0.1 percent to 5% by weight, and more preferably in an amount of from 0.5% to 1.0% by weight, based on the total weight of the composition.

The emulsifiers may be employed in the compositions of the present invention in order to solubilize fatty substances such as fragrance oils or esters, whenever said fatty substances are additionally present in the compositions.

In other embodiments, the compositions of the present invention may contain at least one rheology modifier (also called rheology-modifying agent).

Broadly, the rheology modifier(s) that may be useful in the practice of the present invention include those conventionally used in cosmetics such as polymers of natural origin and synthetic polymers. Rheology modifiers are employed in the compositions of the present invention when it is desired to adjust the viscosity or thickness of the compositions or to achieve a particular composition texture.

Representative rheology-modifying agents that may be used in the practice of the present invention are those other than the at least one film forming polymer of the present invention and include nonionic, anionic, cationic, and amphoteric polymers, and other rheology modifiers such as cellulose-based thickeners (e.g., hydroxyethylcellulose, hydroxypropylcellulose, carboxymethylcellulose, cationic cellulose ether derivatives, quaternized cellulose derivatives, etc.), guar gum and its derivatives (e.g., hydroxypropyl guar, cationic guar derivatives, etc.), gums such as gums of microbial origin (e.g., xanthan gum, scleroglucan gum, etc.), and gums derived from plant exudates (e.g., gum arabic, ghatti gum, karaya gum, gum tragacanth, carrageenan gum, agar gum and carob gum), pectins, alginates, and starches, crosslinked homopolymers of acrylic acid or of acrylamidopropane-sulfonic acid, associative polymers, non-associative thickening polymers, and water-soluble thickening polymers.

In some embodiments, the rheology-modifying agent includes a polymer other than the at least one film forming polymer of the present invention and chosen from nonionic, anionic, cationic and amphoteric amphiphilic polymers.

The rheology-modifying agents may also be chosen from associative celluloses include quaternized cationic celluloses and quaternized cationic hydroxyethylcelluloses modified by groups containing at least one hydrophobic chain, such as alkyl, arylalkyl or alkylaryl groups containing at least 8 carbon atoms, and mixtures thereof.

The alkyl radicals carried by the above quaternized celluloses or hydroxyethylcelluloses may, in various embodiments, comprise from 8 to 30 carbon atoms. The aryl radicals may, for example, denote the phenyl, benzyl, naphthyl or anthryl groups. Representative examples of quaternized alkylhydroxy-ethylcelluloses containing a C8-C30 hydrophobic chain include the products Quatrisoft LM 200®, Quatrisoft LM-X 529-18-A®, Quatrisoft LM-X 529-18B® (C12 alkyl) and Quatrisoft LM-X 529-8® (Ci8 alkyl)

sold by Amerchol and the products Crodacel QM®, Crodacel QL® (C12 alkyl) and Crodacel QS® (Ci8 alkyl) sold by Croda.

Representative examples of nonionic cellulose derivatives include hydroxyethylcelluloses modified by groups comprising at least one hydrophobic chain, such as alkyl, arylalkyl or alkylaryl groups, or their blends, and in which the alkyl groups are, for example, C8-C22 alkyl groups, such as the product Natrosol Plus Grade 330 CS® (C16 alkyls) sold by Aqualon or the product Bermocoll EHM 100® sold by Berol Nobel.

Representative examples of cellulose derivatives modified by alkylphenyl polyalkylene glycol ether groups include the product Amercell Polymer HM-1500® sold by Amerchol.

The rheology-modifying agent is typically present in an amount ranging from about 0.01% to about 10% by weight, in some embodiments from about 0.1% to about 5% by weight, or from about 0.49% to about 1% by weight, based on the total weight of the composition.

In some instances, certain rheology modifiers are also known as gelling agents or thickening agents.

In yet other embodiments, the compositions of the present invention may contain at least one propellant. Propellants can used to deliver the composition as a foam (such as in a mousse product).

Representative examples of propellants include C3 to C5 alkanes such as n-butane, isobutane, isopropane, and propane, dimethyl ether, C2-05 halogenated hydrocarbons, e.g., 1,1-difluoroethane or hydroflurocarbon, difluoroethane, chlorodifluoroethane, chlorodifluoromethane, air (such as compressed air), nitrogen, carbon dioxide, and mixtures thereof. The amount of the propellant can range from about 3 to about 90%, and in some embodiments from about 3 to about 60%, by weight, or such as from about 3 to about 20% by weight, or such as from about 3 to about 10% by weight, or such as from about 3 to about 6%, by weight based on the total weight of the composition, including all ranges and subranges therebetween.

The compositions disclosed herein may take the form of a gel, a mousse such as an aerosol mousse, a spray such as an aerosol spray or a pump spray, a spray gel, a lotion, a tonic, or a cream. The compositions may also be provided as rinse-off or leave-in products, preferably, leave-in products.

In one preferred embodiment, the composition of the present invention is used as a leave-in product.

In another preferred embodiment, the composition of the present invention is used as a hair styling product.

In one particular embodiment, the composition of the present invention is in the form of a gel.

In another particular embodiment, the composition of the present invention additionally contains at least one propellant and is in the form of a mousse.

Thus, in one embodiment, the invention relates to an aqueous gel composition comprising:
  a) from about 0.5% to about 1.88% by weight of sodium bicarbonate;
  b) from about 0.3% to about 1% by weight at least one acid selected from citric acid, lactic acid, and mixtures thereof;
  c) from about 0.6% to about 7.625% by weight at least one film forming polymer;
  d) a cosmetically acceptable carrier selected from water and water/organic solvent mixture;
  e) optionally, at least one emulsifier comprising PEG-hydrogenated castor oil;
  f) optionally, at least one rheology modifier; and g) optionally, at least one neutralizing agent comprising triethanolamine in an amount of from about 0.5% to about 2.5% by weight;

wherein the weight ratio of the at least one bicarbonate (a) to the at least one acid (b) ranges from greater than about 1:1 to about 2:1; and wherein all weights are relative to the total weight of the composition.

In another embodiment, the invention relates to a mousse composition comprising:
a) from about 1.41% to about 1.88% by weight of sodium bicarbonate;
b) from about 0.47% to about 0.94% by weight at least one acid selected from citric acid, lactic acid, and mixtures thereof;
c) from about 1.434% to about 2.29% by weight at least one film forming polymer;
d) a cosmetically acceptable carrier selected from water and water/organic solvent mixture;
e) at least one propellant;
f) optionally, at least one emulsifier comprising PEG-hydrogenated castor oil; and
g) optionally, at least one neutralizing agent at least one neutralizing agent comprising triethanolamine in an amount of from about 0.5% to about 2.5% by weight;

wherein the weight ratio of the at least one bicarbonate (a) to the at least one acid (b) ranges from about 2:1 to about 3:1; and wherein all weights are relative to the total weight of the composition.

In some other embodiments, the cosmetically acceptable carrier in the composition of the present invention comprises at least one volatile organic solvent or compound (VOC) (e.g., in the case of a spray or an aerosol spray). To reduce the amount of VOC (low VOC product), the volatile organic solvent or compound is partially replaced with water. The amount of the volatile organic solvent generally ranges from greater than 0 (e.g., about 0.01%) to about 90%, and in some embodiments from greater than 0 to about 55%, and in some embodiments from greater than 0 to about 2%, by weight, based on the total weight of the composition. It is preferred that the amount of volatile organic solvent does not exceed 55% by weight.

In other embodiments, the composition of the present invention can be a product for making up or enhancing the appearance of keratinous substrates such as hair comprising eyelashes or hair on the human head. One such a product is mascara; another is a hair cosmetic product such as a styling product or an anti-frizz product or hair smoothing/straightening product or a product that provides curl definition.

The compositions of the present invention may be packaged, for example, in a bottle, a spray device such as an aerosol container/can, a pump dispenser or pump spray, a jar, such as those customary in cosmetology.

The compositions may be applied onto keratinous substrates by using the fingers or hand, or by use of a suitable applicator or by directly dispensing the compositions from a device.

Method of Making

The compositions of the present invention are made by combining at least one bicarbonate compound, at least one acid, at least one film forming polymer, at least one cosmetically acceptable carrier, optionally, at least one neutralizing agent, and optionally, at least one auxiliary ingredient, wherein the weight ratio of the at least one bicarbonate compound (a) to the at least one acid (b) is greater than or equal to about 1:1.

In one embodiment, the method of making the cosmetic composition of the present invention comprises the steps of:
a) mixing at least one acid (e.g., citric acid, lactic acid or mixtures thereof) with at least one cosmetically acceptable carrier (e.g., water or a water/organic solvent mixture) to form an acid-carrier mixture;
b) adding at least one bicarbonate compound (e.g., sodium bicarbonate) to the acid-carrier mixture while mixing is continued; and
c) adding at least one film forming polymer to the acid-carrier mixture while mixing is continued; and wherein the weight ratio of the at least one bicarbonate compound (a) to the at least one acid (b) is greater than or equal to about 1:1.

In the above-described method of making, either step (b) or step (c) is conducted after step (a). Preferably, in the above-described method of making, step (a) is followed by step (b), which is then followed by step (c).

In another embodiment, the method of making the cosmetic composition of the present invention comprises the steps of:
a) mixing at least one bicarbonate compound (e.g., sodium bicarbonate) and at least one acid (e.g., citric acid, lactic acid or mixtures thereof) with the at least one cosmetically acceptable carrier (e.g., water or a water/organic solvent mixture) to form a bicarbonate-acid mixture; and
b) adding at least one film forming polymer to the bicarbonate-acid mixture while mixing is continued;

wherein the weight ratio of the at least one bicarbonate compound (a) to the at least one acid (b) is greater than or equal to about 1:1.

In another embodiment, the method of making the cosmetic composition of the present invention comprises:
a) mixing at least one film forming polymer with at least one cosmetically acceptable carrier (e.g., water or a water/organic solvent mixture) to form a polymer-carrier mixture; and
b) adding at least one acid (e.g., citric acid, lactic acid or mixtures thereof) to the polymer-carrier mixture to form an acid-polymer-carrier mixture while mixing is continued; and
c) adding at least one bicarbonate compound (e.g., sodium bicarbonate) to the acid-polymer-carrier mixture while mixing is continued;

wherein the weight ratio of the at least one bicarbonate compound (a) to the at least one acid (b) is greater than or equal to about 1:1.

In one embodiment, at least one alcohol can be added before the at least one film forming polymer is added to any one of the compositions or mixtures in the above-described methods of making. The at least one alcohol is preferably chosen from ethyl alcohol (alcohol denatured) and phenoxy-alcohol.

When the at least one alcohol is added before the at least one film forming polymer is added to any one of the compositions or mixtures in the above-described methods of making, it is possible to achieve compositions having lower viscosities (e.g., as much as 50% lower in viscosity compared to when the alcohol is added after the at least one acid, the at least one bicarbonate compound, and the at least one film forming polymer are combined or mixed.

The at least one bicarbonate compound in any one of the above-described methods of making may be employed in an amount of from about 0.25% to about 9% by weight, such as from about 0.5% to about 2% by weight, relative to the total weight of the composition, including all ranges and subranges therebetween.

The at least one acid in any one of the above-described methods of making may be employed in an amount of from about 0.25% to about 3% by weight, such as from about 0.25% to about 1% by weight, relative to the total weight of the composition, including all ranges and subranges therebetween.

The at least one film forming polymer in any one of the above-described methods of making may be selected from Polyacrylate-2 Crosspolymer, Polyacrylate-32 Crosspolymer, Crotonic Acid/Vinyl C8-12 Isoalkyl Esters/Va/Bis-Vinyldimethicone Crosspolymer, sodium polystyrene sulfonate, carbomer, VP/VA Copolymer, polyquaternium-11, Octylacrylamide/Acrylates/Butylaminoethyl Methacrylate Copolymer, and mixtures thereof.

An ingredient selected from at least one neutralizing agent, at least one auxiliary ingredient, and mixtures thereof may be added to the cosmetic compositions made according to any one of the above-described methods of making.

Methods of Use

An embodiment disclosed herein is a method of making up or enhancing the appearance of keratinous substrates such as hair, involving applying onto the substrates, any one of the compositions of the present invention.

One particular embodiment disclosed herein is a method for styling hair, comprising applying onto the hair, any one of the compositions of the present invention.

The compositions of the present invention may be employed in an effective amount to adequately cover the surface of the fibers of the hair and to achieve a desirable or effective style or shape of the hair as well as a desirable degree of hold. The precise amount of composition to be applied onto the hair will thus depend on the degree of treatment/styling/shaping/hold desired.

Further disclosed herein is the use of the compositions of the present invention for shaping or styling hair and/or retaining a hairstyle.

The hair that has been contacted with the compositions of the present invention may be further styled or shaped by applying heat on the hair using a blow dryer, flat iron, heating implement, or other suitable devices, and/or by combing or brushing or running the fingers through the hair.

One embodiment of the present invention is a method for styling hair comprising (a) providing the composition of the present invention, and (b) providing instructions for applying said composition to the hair.

Instructions for applying the composition of the present invention onto keratin fibers such as hair on the head or eyelashes may comprise directions of use of the composition for the end-user to follow. The end-user may be a consumer or cosmetologist or salon hair dresser. Directions may comprise instructing the end-user to take an amount of the composition in sufficient quantity such that the composition adequately covers the hair fibers and imparts the desired shape or style or hold to the hair fibers. Directions may additionally instruct the end-user to use a device such as a comb, brush (e.g., hair brush or brush wand), flat iron plates or the fingers for shaping or styling the hair or for separating the fibers of the hair. Directions may also additionally instruct the end-user to apply heat to the hair such as by blow drying the hair or using a heating device on the hair.

Instructions for applying the composition of the present invention onto keratin fibers such as hair may appear on the container (such as can, bottle or jar) holding the composition of the present invention or on the box or carton or other packaging comprising the container holding said composition.

It has been surprisingly and unexpectedly discovered that the combination of at least one bicarbonate compound, at least one acid, at least one film forming polymer and a cosmetically acceptable carrier produces a composition that results in satisfactory styling or shaping of hair, including long lasting wear on the hair and faster drying time on the hair compared to other traditional/conventional cosmetic products. It was also surprisingly and unexpectedly discovered that the compositions of the invention did not produce flaking on the hair.

The degree of styling or shaping hold on the hair may be evaluated by assessing the appearance of the hair, or the reduction in frizziness of the hair, or the retention or curl of the hair after contacting the hair with the composition of the invention.

As used herein, the method and composition disclosed herein may be used on the hair that has not been artificially dyed, pigmented or permed or on the hair that has been artificially dyed, pigmented or permed.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result.

EXAMPLES

The following Examples are intended to be non-restrictive and explanatory only, with the scope of the invention being defined by the claims.

The ingredient amounts/concentrations in the compositions/formulas described below are expressed in % by weight, based on the total weight of the composition/formula.

Example I: Formulation Examples

All of the following inventive formulation examples were made according to this method of preparation:

1. Water was added to a beaker and agitation was commenced.
2. Acid was added to the water and mixed until dissolved.
3. Sodium bicarbonate and film forming polymer were added while continuing to mix. (Either the sodium bicarbonate or the polymer was added first before the other).
4. The mixture began to foam and was mixed until homogeneous.
5. If desired, a neutralizing agent was added until the mixture was clear.
6. If desired, auxiliary ingredients and additives were added.

Examples 1-11: Inventive Formulas

Example 1

Gel with Anionic polymer

| INCI Name | Concentration |
|---|---|
| POLYACRYLATE-2 CROSSPOLYMER (FIXATE SUPERHOLD Polymer) | 6.1 |
| FRAGRANCE | 0.3 |
| TRIETHANOLAMINE | 2.5 |
| AMINOMETHYL PROPANOL | 0 |
| PHENOXYETHANOL | 0.7 |
| SODIUM BICARBONATE | 1 |
| SODIUM LAURYL SULFATE | 0.1 |
| CITRIC ACID | 0.5 |
| PEG-40 HYDROGENATED CASTOR OIL | 0.6 |
| ALCOHOL DENAT. | 2 |
| WATER | 86.2 |

Example 2

Gel with Anionic polymer

| INCI name | Concentration |
|---|---|
| POLYACRYLATE-32 (FIXATE DESIGN Polymer) | 3.3 |
| TRIETHANOLAMINE | 1.5 |
| SODIUM BICARBONATE | 1.0 |
| CITRIC ACID | 0.6 |
| WATER | 93.6 |

Example 3

Gel with higher level of anionic polymer

| INCI Name | Concentration |
|---|---|
| POLYACRYLATE-2 CROSSPOLYMER (FIXATE SUPERHOLD Polymer) | 6.1 |
| CARBOMER | 0.5 |
| FRAGRANCE | 0.3 |
| TRIETHANOLAMINE | 2.5 |
| AMINOMETHYL PROPANOL | 0 |
| CAPRYLOYL GLYCINE | 0.2 |
| SODIUM BICARBONATE | 1 |
| SODIUM LAURYL SULFATE | 0.1 |
| PEG-6 | 0.3 |
| CITRIC ACID | 0.6 |
| PEG-40 HYDROGENATED CASTOR OIL | 0.6 |
| ALCOHOL DENAT. | 1.5 |
| WATER | 86.3 |

Example 4

Gel with Anionic polymer

| INCI Name | Concentration |
|---|---|
| TRIETHANOLAMINE | 1.5 |
| SODIUM BICARBONATE | 1 |
| CITRIC ACID | 0.6 |
| WATER | 94.05 |
| SODIUM POLYSTYRENE SULFONATE (FLEXAN II) | 2.85 |

Example 5

Gel with Anionic polymer and Silicone polymer

| INCI Name | Concentration |
|---|---|
| POLYACRYLATE-2 CROSSPOLYMER (FIXATE SUPERHOLD Polymer) | 7.625 |
| FRAGRANCE | 0.3 |
| TRIETHANOLAMINE | 2.5 |
| PHENOXYETHANOL | 0.7 |
| CAPRYLOYL GLYCINE | 0.1 |
| SODIUM BICARBONATE | 2 |
| SODIUM LAURYL SULFATE | 0.125 |
| PEG-6 | 0.3 |
| CITRIC ACID | 1 |
| PEG-40 HYDROGENATED CASTOR OIL | 0.6 |
| ALCOHOL | 1.485 |
| ALCOHOL DENAT. | 0.5 |
| WATER | 81.25 |
| MEK | 0.015 |
| CROTONIC ACID/VINYL C8-12 ISOALKYL ESTERS/ VA/BIS-VINYLDIMETHICONE CROSSPOLYMER (BELSIL P1101) | 1.5 |

Example 6

Gel with Anionic polymer

| INCI Name | Concentration |
|---|---|
| POLYACRYLATE-2 CROSSPOLYMER (FIXATE SUPERHOLD Polymer) | 6.1 |
| FRAGRANCE | 0.3 |
| TRIETHANOLAMINE | 2.5 |
| AMINOMETHYL PROPANOL | 0 |
| CAPRYLOYL GLYCINE | 0.2 |
| SODIUM BICARBONATE | 1 |
| SODIUM LAURYL SULFATE | 0.1 |
| PEG-6 | 0.3 |
| CITRIC ACID | 0.6 |
| PEG-40 HYDROGENATED CASTOR OIL | 0.6 |
| ALCOHOL DENAT. | 1.5 |
| WATER | 86.8 |

Example 7

Gel with Nonionic polymer

| INCI Name | Concentration |
|---|---|
| FRAGRANCE | 0.2 |
| TRIETHANOLAMINE | 1.5 |
| PHENOXYETHANOL | 0.8 |
| AMINOMETHYL PROPANOL | 0 |
| CAPRYLOYL GLYCINE | 0.1 |

-continued

Gel with Nonionic polymer

| INCI Name | Concentration |
|---|---|
| SODIUM BICARBONATE | 1 |
| VP/VA COPOLYMER (LUVISKOL VA 64 W) | 1 |
| CITRIC ACID | 0.5 |
| PEG-40 HYDROGENATED CASTOR OIL | 4 |
| ALCOHOL DENAT. | 2 |
| WATER | 88.41 |
| CARBOMER | 0.49 |

Example 8

Gel with Cationic polymer

| INCI Name | Concentration |
|---|---|
| SODIUM BICARBONATE | 1 |
| POLYQUATERNIUM-11 (GAFQUAT 755) | 0.6 |
| CITRIC ACID | 0.6 |
| WATER | 97.8 |

Example 9

Gel with Amphoteric polymer

| INCI Name | Concentration |
|---|---|
| OCTYLACRYLAMIDE/ACRYLATES/BUTYLAMINO ETHYL METHACRYLATE COPOLYMER (AMPHOMER) | 3 |
| AMINOMETHYL PROPANOL | 0.5 |
| SODIUM BICARBONATE | 1.5 |
| CITRIC ACID | 0.5 |
| WATER | 94.50 |

Example 10

Mousse with Anionic polymer

| INCI Name | Concentration |
|---|---|
| POLYACRYLATE-2 CROSSPOLYMER (FIXATE SUPERHOLD Polymer) | 2.29 |
| FRAGRANCE | 0.188 |
| SODIUM BICARBONATE | 1.88 |
| SODIUM LAURYL SULFATE | 0.094 |
| CITRIC ACID | 0.94 |
| PEG-40 HYDROGENATED CASTOR OIL | 0.353 |
| CAPRYLOYL GLYCINE | 0.094 |
| WATER | 87.503 |
| DIMETHYL ETHER | 2 |
| ISOBUTANE | 2.28 |
| PROPANE | 1.72 |
| PHENOXYETHANOL | 0.658 |

Example 11

Mousse with Anionic Polymer

| INCI Name | Concentration |
|---|---|
| POLYACRYLATE-2 CROSSPOLYMER (FIXATE SUPERHOLD Polymer) | 1.4335 |
| FRAGRANCE | 0.188 |
| PHENOXYETHANOL | 0.658 |
| CAPRYLOYL GLYCINE | 0.094 |
| SODIUM BICARBONATE | 1.41 |
| SODIUM LAURYL SULFATE | 0.0235 |
| CITRIC ACID | 0.47 |
| PEG-40 HYDROGENATED CASTOR OIL | 0.376 |
| PROPANE | 2.58 |
| ISOBUTANE | 3.42 |
| WATER | 89.347 |

Example 12

Gel compositions (with and without a second film forming polymer)

| INCI Names | Example 12-A | Example 12-B |
|---|---|---|
| SODIUM BICARBONATE | 1 | 1 |
| TRIETHANOLAMINE | 2.5 | 2.5 |
| CAPRYLOYL GLYCINE | 0.2 | 0.2 |
| CITRIC ACID | 0.6 | 0.5 |
| FRAGRANCE | — | 1 |
| VP/VA COPOLYMER | — | 0.5 |
| POLYACRYLATE-2 CROSSPOLYMER (FIXATE SUPERHOLD POLYMER) | 6.1 | 7.625 |
| PHENOXYETHANOL | — | 0.7 |
| ALCOHOL DENAT. | 2 | 2 |
| SODIUM LAURYL SULFATE | 0.1 | 0.125 |
| PEG-6 | 0.3 | — |
| PEG-40 HYDROGENATED CASTOR OIL | 0.5 | 1.5 |
| WATER | 86.7 | 82.35 |

The formulas above were tested on hair by applying them on hair of mannequin heads or hair on human heads. The formulas imparted a styling or shaping hold to the hair.

Examples 13-14: Inventive and Comparative Formulas

Example 13

| INCI Name | Inventive formula I | Comparative A | Comparative B | Comparative C |
|---|---|---|---|---|
| SODIUM BICARBONATE | 0.5 | 0.5 | | |
| TRIETHANOLAMINE | 2.5 | 2.5 | 2.5 | 2.5 |
| CAPRYLOYL GLYCINE | 0.2 | 0.2 | 0.2 | 0.2 |
| CITRIC ACID | 0.3 | | 0.3 | |
| FRAGRANCE | 0.3 | 0.3 | 0.3 | 0.3 |
| CARBOMER | 1 | 1 | 1 | 1 |
| POLYACRYLATE-2 CROSSPOLYMER (FIXATE SUPERHOLD Polymer) | 3.05 | — | — | 3.05 |
| ALCOHOL DENATURE | 1.5 | 1.5 | 1.5 | 1.5 |

| INCI Name | Inventive formula I | Comparative A | Comparative B | Comparative C |
|---|---|---|---|---|
| WATER | QS | QS | QS | QS |
| PEG-6 | 0.3 | 0.3 | 0.3 | 0.3 |
| PEG-40 HYDROGENATED CASTOR OIL | 0.6 | 0.6 | 0.6 | 0.6 |

The formulas in Example 13 were tested on hair of mannequin heads. Comparative formulas A, B, and C imparted less hold to the hair compared to the hold provided by the inventive formula. It was also observed that the inventive formula had a clean and natural feel on the hair.

Example 14

Inventive formulas with and without thickener

| INCI Name | Formula II | Formula III | Formula IV |
|---|---|---|---|
| SODIUM BICARBONATE | 1 | 1 | 1 |
| TRIETHANOLAMINE | 2.5 | 2.5 | 2.5 |
| CAPRYLOYL GLYCINE | 0.2 | 0.2 | 0.2 |
| CITRIC ACID | 0.6 | 0.6 | 0.6 |
| FRAGRANCE | 0.3 | 0.3 | — |
| CARBOMER | 0.5 | — | — |
| POLYACRYLATE-2 CROSSPOLYMER (Fixate Superhold Polymer) | 6.1 | 6.1 | 6.1 |
| ALCOHOL DENATURED | 1.5 | 1.5 | 1.5 |
| WATER | QS | QS | QS |
| PEG-6 | 0.3 | 0.3 | 0.3 |
| PEG-40 HYDROGENATED CASTOR OIL | 0.6 | 0.5 | 0.5 |

Formula IV in Example 14 above exhibited the least degree of viscosity among the three inventive formulas but the highest degree of hold on the hair. These results indicate that the degree of viscosity and hold on the hair can be controlled by the use of additional ingredients such as rheology modifiers (carbomer), emulsifier (PEG-40 hydrogenated oil), and fragrance.

Example II: Testing on Hair

Salon Sensory Test Data Results
Test I:
A half-head evaluation of Carbonated gel (inventive formula I in Example 13) vs. Non-Carbonated gel (comparative formula I without sodium bicarbonate and citric acid) was performed on the hair of 8 individuals of fine to medium hair ranging from straight to curly hair. The hair on one side of the head was contacted with the inventive formula, the hair on the other side of the head was contacted with the comparative formula.

The results show that the hair treated with the inventive composition performed better in terms of the degree of hold. The hair treated with the inventive composition was stiffer and harder to separate after drying. The inventive composition also performed better in terms of shine, clean look and feel, faster dry time and added root lift.

Test II:
A half-head evaluation of Carbonated gel (inventive formula in Example 6) vs. Non-Carbonated gel (commercial gel product with no carbonated system) was performed on the hair of 8 individuals of fine to medium hair ranging from straight to curly hair. The hair on one side of the head was contacted with the inventive formula, the hair on the other side of the head was contacted with the commercial gel product. The results show that the inventive composition dried faster on the hair. The hair treated with the inventive composition maintained a cleaner look and feel, with better root lifting.

Mannequin Test Data Results
A half-head evaluation of Carbonated gel (inventive formula I in Example 13) vs. Non-Carbonated gel (comparative formula I without sodium bicarbonate and citric acid) was performed on the hair of a mannequin head. The inventive and the comparative formulas were applied on the hair on the mannequin head using 2.5 g. of each formula.

It was observed that the inventive formula outperformed the comparative formula in that the inventive formula provided volume and root lift. Additionally, after the gels dried on the hair, it was observed that the inventive formula provided more shine and a cleaner feel to the hair when compared to the comparative formula. It was also found that the hair contacted with the inventive formula exhibited more styling/shaping hold and volume and root lift even after running the fingers through the hair.

SEM Evaluation of Hair Swatch:
One gram of the inventive gel, formula I in Example 13 was applied on one gram of a hair swatch. One gram of comparative formula I without sodium bicarbonate and citric acid was applied on one gram of a second hair swatch. Hair strands from the swatches were observed by scanning electron microscopy (SEM), Table Top Microscope HITACHI TM1000. The hair strands contacted with the inventive formula appeared to be fully coated with a film (smooth cuticle surface). The film on the strands contacted with the comparative formula appeared to be uneven and thinner; some parts of the strands were not covered.

Example III

The following inventive example was made by combining Crotonic Acid/Vinyl C8-12 Isoalkyl Esters/Va/Bis-Vinyldimethicone Crosspolymer, Alcohol, Lactic acid and Sodium bicarbonate in a beaker and mixing them together until the mixture was homogenous.

Example 14

BELSIL containing formula*

| INCI | Concentration |
|---|---|
| CROTONIC ACID/VINYL C8-12 ISOALKYL ESTERS/VA/BIS-VINYLDIMETHICONE CROSSPOLYMER | 0.85 |
| ALCOHOL | 0.84 |
| LACTIC ACID | 0.6 |
| SODIUM BICARBONATE | 1.00 |

*The formula can be added to an anhydrous carrier or neutralized before adding to water Example IV: Curl Retention Data The styling/shaping hold properties were tested on curly hair by measuring the percent curl retention on hair swatches at 97% and at 90% relative humidity and over time (from 0 minutes, T0, up to 24 hours, T24 or up to 72 hours, T72).

Designated hair swatches were curled after shampooing and then contacting the swatches with the inventive composition. Other designated hair swatches were also curled after shampooing and contacting the swatches with a comparative composition (commercial product with no carbonated system). Control swatches were curled after shampooing.

TABLE 1

| | Treatment | Baseline | 0 min | 5 min | 15 min | 30 min | 1 hr | 2 hr | 4 hr | 8 hr | 24 hr |
|---|---|---|---|---|---|---|---|---|---|---|---|
| 97% Humidity | | | | | | | | | | | |
| A Shampoo plus inventive composition (Example 1 formula) | AVG % Curl Retention | 100 | 97.19 | 97.19 | 97.19 | 97.19 | 96.63 | 96.63 | 94.94 | 91.57 | 19.10 |
| | SD | 0 | 0 | 0 | 0 | 0 | 1.26 | 1.26 | 3.08 | 3.44 | 10.77 |
| B Shampoo plus comparative composition | AVG % Curl Retention | 100 | 98.88 | 98.88 | 98.88 | 98.88 | 98.88 | 98.31 | 77.53 | 12.36 | 8.47 |
| | SD | 0 | 1.54 | 1.54 | 1.54 | 1.54 | 1.54 | 1.54 | 12.72 | 2.35 | 3.20 |
| C Shampoo only | AVG % Curl Retention | 100 | 84.55 | 71.91 | 51.78 | 25.56 | 11.05 | 8.71 | 7.77 | 7.30 | 7.30 |
| | SD | 0 | 8.47 | 6.88 | 7.83 | 13.85 | 2.29 | 1.45 | 2.11 | 1.78 | 1.78 |

SD = standard deviation

The results in Table 1 above show that from T0 to T4 (4 hours), the percentage of curl retention for swatches subjected to treatments A (invention) and B (comparative) were significantly higher than the percentage of curl retention for those subjected to treatment C (shampoo only).

At T8 hour, the percentage of curl retention for swatches subjected to treatment A was significantly higher than the percentage of curl retention for those subjected to treatments B and C.

For treatment A, the decrease in the percentage of curl retention from T0 to T8 was significantly less than the decrease in the percentage of curl retention of the swatches subjected to treatments B and C in the same time period.

The results in Table 2 above show that from T0 to T8 (8 hours), the percentage of curl retention for swatches subjected to treatments D, E (inventions) and F (comparative) were significantly higher than the percentage of curl retention for those subjected to treatment G (shampoo only). At T24 hour to T72 hour, the percentage of curl retention for swatches subjected to treatments D and E were significantly higher than the percentage of curl retention for those subjected to treatments F and G. For treatments D and E, the decrease in the percentage of curl retention from T0 to T72 was significantly less than the decrease in the percentage of curl retention of the swatches subjected to treatments F and G in the same time period.

Example V: Drying Time and Wear on Hair

An inventive formula and a comparative formulas were tested for drying time; the inventive formula contained: 0.5% by wt sodium bicarbonate, 0.25% by wt citric acid, 5.163% by wt VP/dimethylaminoethylmethacrylate and

TABLE 2

| | Treatment | Baseline | 0 min | 5 min | 15 min | 30 min | 1 hr | 2 hr | 4 hr | 8 hr | 24 hr | 48 hr | 72 hr |
|---|---|---|---|---|---|---|---|---|---|---|---|---|---|
| 90% humidity | | | | | | | | | | | | | |
| D Shampoo plus inventive composition (Ex 12-A) | AVG % Curl Retention | 100 | 95.79 | 95.79 | 95.79 | 95.79 | 95.32 | 95.32 | 94.85 | 94.85 | 83.61 | 78.00 | 73.31 |
| | SD | 0 | 1.54 | 1.54 | 1.54 | 1.54 | 2.29 | 2.29 | 2.76 | 2.76 | 11.84 | 15.12 | 19.68 |
| E Shampoo plus inventive composition (Ex 12-B) | AVG % Curl Retention | 100 | 96.72 | 96.25 | 96.25 | 96.25 | 95.79 | 95.32 | 95.32 | 90.64 | 73.78 | 62.08 | 56.93 |
| | SD | 0 | 1.15 | 1.45 | 1.45 | 1.45 | 2.35 | 2.29 | 2.29 | 5.80 | 10.76 | 7.27 | 8.08 |
| F Shampoo plus comparative composition | AVG % Curl Retention | 100 | 96.72 | 96.72 | 96.72 | 96.25 | 95.79 | 95.32 | 93.45 | 86.42 | 34.93 | 11.99 | 10.11 |
| | SD | 0 | 2.11 | 2.11 | 2.11 | 2.29 | 1.54 | 2.29 | 4.59 | 9.80 | 21.64 | 3.40 | 3.08 |
| G Shampoo only | AVG % Curl Retention | 100 | 68.16 | 63.95 | 50.84 | 41.95 | 27.43 | 23.22 | 18.07 | 15.73 | 13.86 | 14.33 | 14.33 |
| | SD | 0 | 1.45 | 2.11 | 3.87 | 6.57 | 5.45 | 4.23 | 4.13 | 5.62 | 4.92 | 5.26 | 5.26 |

SD = standard deviation acrylates/steareth-20 methacrylate crosspolymer, 0.8% by wt triethanolamine, 1% by wt PEG-40 hydrogenated castor oil, 2% by wt denatured alcohol, 0.784% by wt phenoxyethanol, auxiliary ingredients, organic solvents, and water. The comparative formula did not contain sodium bicarbonate and citric acid. Equal amounts of each formula were applied on mannequin hair in a half-head study. Surprisingly and unexpectedly after 1.5 hour, the hair treated with the inventive formula was noticeably drier to the touch compared to the hair treated with the comparative. In another test, it was found that the inventive formula dried on the hair in half the time it took for the comparative to dry. These results indicate that the inventive formula formed a film on the hair much more quickly which is a desirable cosmetic attribute.

It was also surprisingly and unexpectedly observed that the wear on the hair of the inventive formula was longer compared to that of the comparative over a period of one week which the means that the inventive formula had longer lasting hold properties.

It will be apparent to those skilled in the art that various modifications and variations can be made in the delivery system, composition and methods of the invention without departing from the spirit or scope of the invention. Thus, it is intended that the present invention cover the modifications and variations of this invention provided that they come within the scope of the appended claims and their equivalents.

What is claimed is:

1. A cosmetic composition comprising:
    i) the reaction product of:
        a) about 0.25 wt. % to about 9 wt. % of at least one bicarbonate compound;
        b) about 0.25 wt. % to about 3 wt. % of at least one acid selected from the group consisting of citric acid, lactic acid, and mixtures thereof;
            wherein the weight ratio of the at least one bicarbonate compound (a) to the at least one acid (b) is from about 1:1 to about 3:1;
    ii) about 0.5 wt. % to about 10 wt. % of at least one anionic film forming polymer; and
    iii) about 10 wt. % to about 98 wt. % of at least one cosmetically acceptable carrier;
        wherein all weights are relative to the total weight of the composition, the composition does not exhibit phase separation, is free of plant extracts and ceramides, and the composition is not a foam.

2. The composition of claim 1, wherein the cosmetically acceptable carrier is selected from water, organic solvents, and mixtures thereof.

3. The composition of claim 2, wherein the cosmetically acceptable carrier comprises water and at least one organic solvent selected from alcohols.

4. The composition of claim 1, wherein the weight ratio of the at least one bicarbonate compound (a) to the at least one acid (b) is from about 1.5:1 to about 3:1.

5. The composition of claim 1, wherein the weight ratio of the at least one bicarbonate compound (a) to the at least one acid (b) is from about 2:1 to about 3:1.

6. The composition of claim 1, wherein the at least one bicarbonate (a) is sodium bicarbonate.

7. The composition of claim 1, wherein the composition further comprises at least one neutralizing agent.

8. The composition of claim 7, wherein the at least one neutralizing agent is selected from alkali metal carbonates other than bicarbonate compounds, alkali metal phosphates, organic amines, hydroxide base compounds, and mixtures thereof.

9. The composition of claim 1, wherein the composition is a hair styling composition.

10. The composition of claim 1, wherein the composition is free of surfactants.

11. A hair cosmetic composition consisting essentially of:
    i) the reaction product of:
        a) 0.5 wt. % to about 4 wt. % of sodium bicarbonate;
        b) 0.25 wt. % to about 2 wt. % of at least one acid selected from the group consisting of citric acid, lactic acid, and mixtures thereof;
            wherein the weight ratio of sodium bicarbonate (a) to the at least one acid (b) ranges from about 1:1 to about 3:1
    ii) 0.5 wt. % to about 10 wt. % of at least one anionic film forming polymer;
    iii) a cosmetically acceptable carrier selected from the group consisting of water, organic solvents, and mixtures thereof;
    iv) optionally, at least one emulsifier; and
    v) optionally at least one rheology modifier;
        wherein all weights are relative to the total weight of the composition, the composition is not a foam, does not exhibit phase separation, and is free of ceramides.

12. A cosmetic composition consisting essentially of:
    i) the reaction product of:
        a) about 0.25 wt. % to about 9 wt. % of at least one bicarbonate compound;
        b) about 0.25 wt. % to about 3 wt. % of at least one acid selected from the group consisting of citric acid, lactic acid, and mixtures thereof;
            wherein the weight ratio of the at least one bicarbonate compound (a) to the at least one acid (b) is from about 1:1 to about 3:1;
    ii) about 0.5 wt. % to about 10 wt. % of at least one anionic film forming polymer;
    iii) about 10 wt. % to about 98 wt. % of at least one cosmetically acceptable carrier;
    iv) about 0.01 wt. % to about 5 wt. % of at least one neutralizing agent that is an alkanolamine;
    v) optionally, at least one emulsifier; and
    vi) optionally, at least one rheology modifier;
        wherein all weights are relative to the total weight of the composition;
    and the compositions does not exhibit phase separation and is free of ceramides.

13. The cosmetic composition of claim 12, wherein the alkanolamine is selected from the group consisting of monoethanolamine, triethanolamine, 2-amino-2-methyl-1-propanol, and mixtures thereof.

14. The cosmetic composition of claim 13, wherein the alkanolamine is triethanolamine.

15. The cosmetic composition of claim 12 comprising the at least one emulsifier of (v) and the at least one rheology modifier of (vi).

16. The composition of claim 12, wherein the weight ratio of the at least one bicarbonate compound (a) to the at least one acid (b) is from about 1.5:1 to about 3:1.

17. A method of making up or enhancing the appearance of keratinous substrates comprising applying to the keratinous substrates, topically, a composition according to claim 1.

18. A method of styling or shaping hair comprising applying to the hair, topically, a composition according to claim 1.

19. A method of styling hair comprising (a) providing the composition of claim 1, and (b) applying the composition to hair.

20. A method of making the composition of claim 1 comprising the steps of:
- a) mixing the at least one acid with the at least one cosmetically acceptable carrier to form an acid-carrier mixture;
- b) adding the at least one bicarbonate compound to the acid-carrier mixture while mixing is continued;
- c) adding the at least one film forming polymer to the acid-carrier mixture while mixing is continued;
- d) optionally, adding at least one organic solvent selected from alcohols before step c); and
- e) mixing until the composition is not a foam.

\* \* \* \* \*